United States Patent [19]
Allison

[11] Patent Number: 5,888,809
[45] Date of Patent: Mar. 30, 1999

[54] HAMSTER EF-1α TRANSCRIPTIONAL REGULATORY DNA

[75] Inventor: Daniel S. Allison, Seattle, Wash.

[73] Assignee: ICOS Corporation, Bothell, Wash.

[21] Appl. No.: 847,218

[22] Filed: May 1, 1997

[51] Int. Cl.$^6$ .............................. C12N 5/10; C12N 1/00; C12N 15/11; C12N 15/63
[52] U.S. Cl. ...................... 435/325; 435/243; 435/320.1; 435/410; 536/23.1; 536/23.5; 536/24.1
[58] Field of Search ................... 536/24.1, 23.1, 536/23.5; 435/320.1, 325, 243, 410

[56] References Cited

U.S. PATENT DOCUMENTS

| | | | |
|---|---|---|---|
| 5,266,491 | 11/1993 | Nagata et al. | 435/320.1 |
| 5,650,294 | 7/1997 | Kurth et al. | 435/69.1 |

FOREIGN PATENT DOCUMENTS

| | | |
|---|---|---|
| 2051085 | 3/1993 | Canada . |
| WO 91/09955 | 7/1991 | WIPO . |
| WO 92/20808 | 11/1992 | WIPO . |
| WO 94/12650 | 6/1994 | WIPO . |

OTHER PUBLICATIONS

Mizushima and Nagata, *Nucleic Acids Research* 18:5322 (1990).

Ng et al, J. of Biol Chem, Oct. 27, 1995, vol. 270 (43): pp. 25850–25858.

Mitchell et al, Science, Jul. 28, 1989, vol. 245: pp. 371–378.

Boshart et al., *Cell* 41:521 (1985).

Boulikas, *Crit.Rev.Euk. Gene Exp.* 4:117–321 (1994).

Dijkema et al., *EMBO, J.* 4:761 (1985).

Gorman et al., *Proc. Nat'l.Acad.Sci.* (USA), 79:6777 (1982b).

Hayashi et al., *J.Biochem.* 106:560–563 (1989).

Sarver et al., *Mol.Cell.Biol.*, 1:486 (1981).

Uetsuki et al., *J.Biol.Chem.* 264:5791–5798 (1989).

*Primary Examiner*—Terry McKelvey
*Attorney, Agent, or Firm*—Marshall, O'Toole, Gerstein, Murray & Borun

[57] ABSTRACT

The present invention relates to regulatory DNA sequences derived from the hamster EF-1α gene. The invention further encompasses expression constructs comprising regulatory DNA of the invention, host cells transformed or transfected with the regulatory DNA and methods of increasing gene transcription utilizing the regulatory DNA. Expression constructs comprising regulatory DNA of the invention operably linked to specific gene sequences are also comprehended.

29 Claims, No Drawings

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
( A ) LENGTH: 3678 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

```
ACTAGTTCCA  AAGATGAATT  ACTAACCAGT  GTTTCCAAGG  AAATAAATGA  AAGCAGAGAG      60

ATTAGTTCTA  TTGCTAGTGT  TTCATTTTCG  TATATTTCTT  ACAATTTCTC  TTGTTACAAA     120

TAGGCACTAG  GGTATCAAGA  TAATTTTAAC  GACTGGCTGA  GAACCCTAGA  AAATCTCTGT     180

GAAAAGGGA   TTTGTGAAAT  GAGAGAGGGT  AATGTGGCCA  TTATAGAAAA  GGCTTTTGTG     240

TGCCTTGCAT  GCATAGACCC  TGTGTTTGAT  CTCTTAACAC  CCTCCTTGAC  CAGAAAAAGC     300

TTCTGTGGAT  AGAAAATGAT  TAGTTATATA  TACTTTTAGG  GAAACGTAGT  TCTGGATTCT     360

TTGGTTACAA  TTAACAGAAT  TAAGTGCAAA  CAAAGCCAGA  AACCTCCTGA  TAAATGAGAA     420

AACCTGCTTG  TAGAAGGTTG  TAAGGCTCTG  TAATATAGGA  ATTAGGAGAA  AAGAAACCTG     480
```

```
TGTGGTGGGG  CACGTCTGTA  ATCCCAGCAT  TGGGAAGTAG  AGGTAGAAGA  TTAGAAATCA      540
AAGGCCAGCC  TCAGCAACAC  AGTGAGTTTG  AGGCCACCCT  GAACTACATC  AGGTTCTGTC      600
TCCTTTCTTT  TTTTTTTTT   TTTCTTTTCT  TTTTTGGTT   TCTCTGTGTA  GTTTGGAGC       660
CTATCCTGGC  ACTAGCTCTG  AAGAGCAGGC  TGGCCTCGAA  CTCAGAGATC  AGCCAGCCTC      720
TGCTGGGATT  AAAGGTATGC  ACCACCAACG  CCCCAGGTTT  TGTCTCAAAC  AAACAAAAAT      780
AACATCAGGA  GGTGGTGAGA  GGGCTCAGTG  GTCACAGGCA  TTCTCTGCAA  AGCCTGACTC      840
TGAGTTGGAT  CCTTTAGAGC  TACATGGTTG  AGGGAAGAGA  ACTGACTCCT  GGAAGGTGTC      900
CTCTGGTCCC  CACACATAGC  TATACACAGC  ATGTGCATTC  ACACACACTA  AATAATGCTA      960
TTTTTAAAAA  AATTAAAAAC  AACAACAGTT  TGGGTTGTGA  AAACTAGAAC  TAGATAATAG     1020
GTAAGAATCA  AGTATCATGT  AAATTTGCTT  TCAACTCATC  CCAAAATTTG  TTTTATATTT     1080
CAGTTTTTTT  CCTTCCTAGC  TTGACTGTGG  AGTCTTGTCC  GGAAGCAAAT  AGTTCCTTTG     1140
CAGATCCCAC  ATGTGGACAC  CGGACAGTAG  GTCCTCAAAT  GCTCCTTATT  AGGTTGGTTC     1200
AATAATATCA  ATTGTTTGTT  ACTAGGCAGT  GATGTTGTAC  ATCTGGAGGA  GATCTCTTGA     1260
GCCCATAATC  AGGTTATTAG  GAATAAATAC  TCTAAGGCTA  AAAATGTAGC  TTAGTGATAA     1320
GAGTGCTTGC  CTGGTGTGCT  GAGACCCTCG  GTTCCATCTC  CACAACCCCA  TATTCCATTA     1380
CAAAATACCT  TTTCACCGTC  CCTAGCATTA  AGAAACAAAA  CAACAAAGAA  GTTTTCTTT      1440
CTTCTGAGAT  CCTGCCCGGA  GAGGCATTTA  AAACTGGCCA  GGGCCAAAAA  AAAAAAAAA      1500
AAAAGAAAAA  AAAGAAAAGA  AAACAGGCTA  GGGCCGGCAT  GGTGGCGCAC  GCCTTTAATC     1560
CCAGCACGCA  GGAGGCAGAG  GCAGGGCGGA  TCTCTGTGAG  TTTGAGGTCA  GCCTGGTCTA     1620
CCTAGTGAGT  TTCAGGGCAC  CCAGGGCTAA  AGAGACTGTC  TCAAAAACAA  AACAGCCACA     1680
CAATCAGAAC  CACAGCAAAA  CGCAGTTATG  ATCCTTGGAA  CTGTAGGAAT  GACAAGCATT     1740
TAAATAATAG  GACGAGCCAT  TTTTGAGAAG  CTCTGATTTC  ACAAGTGTCA  GGGATGGGCT     1800
CTGGGCGAGT  AAGATTGCTA  ATGCTGGCCT  CTAAATGAGA  CCACGTGGAG  TTGATTAGAT     1860
TCTTTTCATG  TTCCTCGTGC  TCTATCAAAT  AACTGTACCC  AAATACACAC  ACACACACAC     1920
ACACACACAA  TGCGCGCACA  CACAAAATCC  TTTTTTAGCT  TAAGAAGCCC  AGAATCAGAA     1980
GTAAAGCTAA  CTGTGGGACT  TAAGTATTAT  TCTGAACGGA  ACTCCCAGGG  CGTGAAGCGC     2040
GCTTCAGGCT  TCCAGAGAAG  CAGCTGGCGC  TGGATGGAAT  GAACCAAGAG  GCCAGCACAG     2100
GGGCAGATCC  GTCGAGCTCT  CGGCCACCGA  GCTGAGCCCT  TAGGTTCTGG  GGCTGGGAAG     2160
GGTCCCTAGG  ATTGTGCACC  TCTCCCGCGG  GGACAAGCA   GGGGATGGCG  GGGCTGACGT     2220
CGGGAGGTGG  CCTCCACGGG  AAGGGACACC  CGGATCTCGA  CACAGCTTG   GCAGTGGAGT     2280
CAGGAAGGGT  AGGACAGATT  CTGGACGCCC  TCTTGGCCAG  TCCTCACCGC  CCCACCCCCG     2340
ATGGAGCCGA  GAGTAATTCA  TACAAAAGGA  GGGATCGCCT  TCGCCCTGG   GAATCCCAGG     2400
GACCGTCGCT  AAATTCTGGC  CGGCCTCCCA  GCCCGGAACC  GCTGTGCCCG  CCAGCGCGG      2460
CGGAGGAGC   CTGCGCCTAG  GGCGGATCGC  GGGTCGGCGG  GAGAGCACAA  GCCCACAGTC     2520
CCCGGCGGTG  GGGGAGGGGC  GCGCTGAGCG  GGGGCCCGGG  AGCCAGCGCG  GGGCAAACTG     2580
GGAAAGTGGT  GTCGTGTGCT  GGCTCCGCCC  TCTTCCCGAG  GGTGGGGGAG  AACGGTATAA     2640
AAGTGCGGTA  GTCGCGTTGG  ACGTTCTTTT  TCGCAACGGG  TTTGCCGTCA  GAACGCAGGT     2700
GAGTGGCGGG  TGTGGCCTCC  GCGGGCCCGG  GCTCCCTCCT  TTGAGCGGGG  TCGGACCGCC     2760
GTGCGGGTGT  CGTCGGCCGG  GCTTCTCTGC  GAGCGTTCCC  GCCCTGGATG  GCGGGCTGTG     2820
CGGGAGGGCG  AGGGGGGGAG  GCCTGGCGGC  GGCCCCGGAG  CCTCGCCTCG  TGTCGGGCGT     2880
```

| | | | | | |
|---|---|---|---|---|---|
|GAGGCCTAGC|GTGGCTTCCG|CCCCGCCGCG|TGCCACCGCG|GCCGCGCTTT|GCTGTCTGCC|2940|
|CGGCTGCCCT|CGATTGCCTG|CCCGCGGCCC|GGGCCAACAA|AGGGAGGGCG|TGGAGCTGGC|3000|
|TGGTAGGGAG|CCCCGTAGTC|CGCATGTCGG|GCAGGGAGAG|CGGCAGCAGT|CGGGGGGGGG|3060|
|ACCGGGCCCG|CCCGTCCCGC|AGCACATGTC|CGACGCCGCC|TGGACGGGTA|GCGGCCTGTG|3120|
|TCCTGATAAG|GCGGCCGGGC|GGTGGGTTTT|AGATGCCGGG|TTCAGGTGGC|CCCGGGTCCC|3180|
|GGCCCGGTCT|GGCCAGTACC|CCGTAGTGGC|TTAGCTCCGA|GGAGGGCGAG|CCCGCCCGCC|3240|
|CGGCACCAGT|TGCGTGCGCG|GAAAGATGGC|CGCTCCCGGG|CCCTGTAGCA|AGGAGCTCAA|3300|
|AATGGAGGAC|GCGGCAGCCC|GGCGGAGCGG|GGCGGGTGAG|TCACCCACAC|AAAGGAAGAG|3360|
|GGCCTTGCCC|CTCGCCGGCC|GCTGCTTCCT|GTGACCCCGT|GGTGTACCGG|CCGCACTTCA|3420|
|GTCACCCCGG|GCGCTCTTTC|GGAGCACCGC|TGGCCTCCGC|TGGGGAGGG|GATCTGTCTA|3480|
|ATGGCGTTGG|AGTTTGCTCA|CATTTGGTGG|GTGGAGACTG|TAGCCAGGCC|AGCCTGGCCA|3540|
|TGGAAGTAAT|TCTTGGAATT|TGCCCATTTT|GAGTTTGGAG|CGAAGCTGAT|TGACAAAGCT|3600|
|GCTTAGCCGT|TCAAAGGTAT|TCTTCGAACT|TTTTTTTAA|GGTGTTGTGA|AAACCACCGC|3660|
|TAATTCAAAT|CCAACATG| | | | |3678|

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

AGGCACAGTC GAGGCTGATC                                                       20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

TTCCAGGGTC AAGGAAGGCA                                                       20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GCCACCTGAT CTACAAATGT                                                       20

( 2 ) INFORMATION FOR SEQ ID NO:5:

( i ) SEQUENCE CHARACTERISTICS:
        ( A ) LENGTH: 20 base pairs
        ( B ) TYPE: nucleic acid (C) STRANDEDNESS: single
(D) TOPOLOGY: linear (i i) MOLECULE TYPE: DNA (x i) SEQUENCE DESCRIPTION: SEQ ID NO:5:

GAGATACCAG CCTCAAATTC    20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:6:

ATGTGACCAT CATTGATGCC    20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:7:

GTGACTTTCC ATCCCTTGAA    20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:8:

GTTGGAATGG TGACAACATG    20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:9:

CAGGTTTTAA AACACCAGTC    20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA ( x i ) SEQUENCE DESCRIPTION: SEQ ID NO:10:

AATGACCCAC CAATGGAAGC 20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

ACAGCAACTG TCTGCCTCAT 20

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

GTAAAACGAC GGCCAGT 17

( 2 ) INFORMATION FOR SEQ ID NO:13:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

GGAAACAGCT ATGACCATG 19

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

AATTAACCCT CACTAAAGGG 20

( 2 ) INFORMATION FOR SEQ ID NO:15:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

GTTAATACGA CTCACTATAG GGC 23

( 2 ) INFORMATION FOR SEQ ID NO:16:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

G G C G G G         6

( 2 ) INFORMATION FOR SEQ ID NO:17:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

G G G C G G         6

( 2 ) INFORMATION FOR SEQ ID NO:18:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

T G A C G Y M R         8

( 2 ) INFORMATION FOR SEQ ID NO:19:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

T G G C N N N N N K C C R         1 3

( 2 ) INFORMATION FOR SEQ ID NO:20:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

G A T C G C G G C C   G C G T T T A A A C   G G A T C C         2 6

( 2 ) INFORMATION FOR SEQ ID NO:21:

( i ) SEQUENCE CHARACTERISTICS:
        ( A ) LENGTH: 26 base pairs
        ( B ) TYPE: nucleic acid (C) STRANDEDNESS: single
(D) TOPOLOGY: linear (ii) MOLECULE TYPE: DNA (xi) SEQUENCE DESCRIPTION: SEQ ID NO:21:

AATTGGATCC GTTTAAACGC GGCCGC                                                                26

(2) INFORMATION FOR SEQ ID NO:22:

(i) SEQUENCE CHARACTERISTICS:
    (A) LENGTH: 77 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:22:

CGTTTAGTGA ACCGTCAGAT CTACATAACA ACATTCCTCC TCTAAAGAAG CCCCAAGCTT            60

GATATCTGCA GAATTCT                                                          77

(2) INFORMATION FOR SEQ ID NO:23:

(i) SEQUENCE CHARACTERISTICS:
    (A) LENGTH: 85 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:23:

CTAGAGAATT CTGCAGATAT CAAGCTTGGG GCTTCTTTAG AGGAGGAATG TTGTTATGTA            60

GATCTGACGG TTCACTAAAC GAGCT                                                 85

(2) INFORMATION FOR SEQ ID NO:24:

(i) SEQUENCE CHARACTERISTICS:
    (A) LENGTH: 66 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:24:

AGTTCAGTCG ACGGCGCGCC AACCCGGGAA TCCGGACGGG ATCTATACAT TGAATCAATA            60

TTGGCA                                                                      66

(2) INFORMATION FOR SEQ ID NO:25:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:25:

ATGTCAGGAT CCACGCGGAA CTCCATATAT GGGCTATGAA CT                               42

(2) INFORMATION FOR SEQ ID NO:26:

(i) SEQUENCE CHARACTERISTICS:
    (A) LENGTH: 19 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:26:

GGCTTAGCTC CGAGGAGGG  19

(2) INFORMATION FOR SEQ ID NO:27:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:27:

CGTGACAAGC TTGGTTTTCA CAACAC  26

(2) INFORMATION FOR SEQ ID NO:28:

(i) SEQUENCE CHARACTERISTICS:
(A) LENGTH: 4263 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:28:

| | | | | | | |
|---|---|---|---|---|---|---|
| TGAATATTAC | CCCTAACACC | TGCCACCCCA | GTCTTAATCA | GTGGTGGAAG | AACGGTCTCA | 60 |
| GAACTGTTTG | TCTCAATTGG | CCATTTAAGT | TTAATAGTGA | AAGACTGGTT | AATGATAACA | 120 |
| ATGCATCGGA | AAACCTTCAG | GAGGAAAGGA | GAATGTTTTG | TGGAACATTT | TTGTGTGTGT | 180 |
| GGCAGTTTTA | AGTTATTAGT | TTTCAAAATC | AGTACTTTTT | AATGGAAACA | ACTTGACCAA | 240 |
| AAATCTGTCA | CAGAATTTTG | AGACCCATTA | AAATACAAGT | TAATGAGAA | GTCTGTCTCT | 300 |
| GTTAATGCTG | AAGTCATTAC | TAAGTGCTTA | GCTTAGCAAG | GTATGTGGAT | GCCCATTTGT | 360 |
| GTTCCAAGGG | ATTGGACTGT | TCATCAGGAC | CCAGAGCTGA | GTTTCAAGGG | CTCAAGAGAT | 420 |
| GGCTTATTAC | CTGTGGGTGT | CTTGAAGGTT | CTGGTTGGGA | CAAATTAGGA | ATGTTTTGG | 480 |
| CAGACATGGT | GACTACCTTC | ATCTGGGTGA | GTTCAGTTGA | TTTGTCTTGA | GCCTTGGGG | 540 |
| TTTACACAAG | TAAATGACAT | CATACAGTTA | GTGTATTGTT | AGTGAATATT | AATATATGAG | 600 |
| GCAGGCTTTG | CTCTAGCAAT | TTTAGAACTA | GTTTTCAGGA | AAGGGTTCAT | CTTGTGCATT | 660 |
| GGATGTTTGA | TTCTATCACT | TAGAGTTTAA | ACTGAAAGTG | CTCAAGAGGT | TTTATTTAGG | 720 |
| CTGGATATA | AATAAGCCTT | TCTGTAGCTT | GTAATGGTAT | CAGGAATTTA | AAAGGCCATC | 780 |
| TGGGGCACAA | AGATTAAGCA | GAAAAGGTAG | AAGGTGAGAT | TGGGGACTT | TGAGTACTTC | 840 |
| ACACACTTTA | ATGTGTGAGT | GCTTTAGTGC | ATATAGTACA | ACTGCCAGAT | AAGGGCATCC | 900 |
| ACATCTGATT | GTTTGGAAGG | CACCTTGTGG | TTTCTGGGAA | TTCAGAATTG | GGAGAAAAAT | 960 |
| GCTCCCAACC | GCTGAAGCCC | TTGGTAATCT | GCAGGGTGTT | TATTTAGCAG | GAGATAAGGA | 1020 |
| CAAAAGTTA | TAGTGTGGAG | TTGGTTGAGT | TGGTAGATGT | CATTACAACA | GGTGGTCTTA | 1080 |
| AATTGGGTTA | GGAGTCACTT | TGAAATACCT | GGGCCATAAG | CAAAGTGGCA | TTTTCACCTT | 1140 |
| TCAGGAGAAA | CTGGTACACT | TATCCATTCT | ATAGTGCATG | CTTGTTCAAT | TGGGCTGATG | 1200 |
| ACTAAACCGG | TGACTAAAGG | TTTGTCAGTA | TAAATGGATG | GGTTGTAGGC | AGACGGTGAG | 1260 |

| | | | | | | |
|---|---|---|---|---|---|---|
| GAATTACTAT | ACCTGCAAGG | AGTCATTGCC | TGATCTGCCT | GGAAAGGGGC | AGGATTGAGT | 1320 |
| CTCAGAACGT | GTACACCATA | GGATATGGAA | AAATTTGTCA | CGCCTAGCAT | TCAACTTAGT | 1380 |
| GGTGTAGCGC | CACCTACTGG | CACTTAAAAA | GCTTAGCATA | GAGGAGCATG | TGTGTTAGGA | 1440 |
| GCTCGGATGG | GATCCAGGGC | CTCAAGGTTT | GCATGTAAAT | AAAAGCCCTT | TACCAAATTA | 1500 |
| ACTACATACC | AGCATACATC | AGTCCTTTAG | TGTTGAAAAA | CAGAAGGGAA | AGCTAATATA | 1560 |
| TATAGTGCTT | GCTTTATTTA | AGTCTAGCTG | ATTACGTGTT | TGGTTGCCAG | TGTGACTAGT | 1620 |
| CTGGAGTTGA | ATTTGTCCTC | AGACACGTAA | AATGGAATTT | GGGATTCACA | ACACTCTAGT | 1680 |
| ATGAGGGACC | TAATGGCCTG | TACCAGGCAC | AAACGTGTCT | ATAAACTACA | CAAAACGAAG | 1740 |
| GAATTTACAG | GAATTAGGAA | GGTATTCTTA | ACATTAAAAC | ATTATGGGCA | TTTTAAAAAA | 1800 |
| AGCTTTGACA | GGATTTCTTT | GTCATGGCTG | TCCTGGAGCT | AGTTGTGTAG | ACCAGGCTGG | 1860 |
| GCTGAAATCT | TGTCTGCCTG | CCTGGCTTGG | ACACTTTTTT | ATTATGTATA | CAACATTCTG | 1920 |
| CTTCCATGTA | TATCTGCACA | TTAGAAGACG | GCACCAGATC | TCCTAATGGA | TGGTTGTGAG | 1980 |
| CCACCATGTG | GTTGCTGGGA | ATTGAACTCA | GGACCTCTGG | AAGAGCAGTG | CTCTTAACCT | 2040 |
| CTGAGCCATC | TCCAGCCCCA | GCTTGGGCAC | ATTTTAATG | GCTGGGAAAT | CAAACCCCCT | 2100 |
| AGGCCTTCTG | TCAGTAATGA | AGGGCTTTTG | GCTACCGAGA | GTAGGATTTA | AGGTTATTCG | 2160 |
| GAGCTGCAGG | TCTGCCTCAG | TGCAGGTTTG | GGAGTCCAGC | ATCTTAGAAA | ATGCAGTGAA | 2220 |
| GCCAAGCTGA | GCTATATTTT | GTTTAAAAAA | AAAATAAGTG | GGTAAAGTGC | TGCTGAGCCT | 2280 |
| GATGACCAAG | CTGGGACACA | AGTAGAAGAA | CATAGGCCAA | TGCTCTATAT | TAAAAGCATG | 2340 |
| GGTCATTTTT | AATGCTCTTG | AGAAGGCTAT | GCCTACACTA | CTCTCAGCCA | CCGCAGCGTG | 2400 |
| TTTAAATTAA | ACTAGTTTGG | AAATTTTCTT | TGGGGGTAAG | CTATTTAACC | TAGTGCCTTG | 2460 |
| GCAGGTATAC | TACTGAACTC | TCCTCCTCAT | TCCTTTTTGT | TTTTTAAGAA | TTTCAGTCAG | 2520 |
| GCTCAGGCAG | CCCTTAAACT | TGTGATTAAG | CCTGAGAACA | GTTACGATTA | TGAGCCTATT | 2580 |
| AGTATACCGA | TCAATATGTG | AATTTTTTG | GGATGGGGGT | CAGGCCTCCC | TGCCTCCCAA | 2640 |
| ATACTGGGAC | TAAAGGCTGC | ACCACCACAA | CCTGGCTCTT | GAAATACTTT | TCTACATTTT | 2700 |
| TTGGGGGGCA | TGGGTGGGAG | AGCAGGGTTT | CTCTGTATTA | GCCCTGGCTC | TCCTGGAACT | 2760 |
| CTGTAGACCA | GGCTATTCTT | GAGCTCAGAT | TAGCCTGTCT | CTGCCTCCTA | AATTCTGGGA | 2820 |
| TTAAAGGTGT | GTGCTACTGC | TGCCTGGCTA | CAAAGACATT | TTTTTTTTC | TTAAATTTAA | 2880 |
| AAACAAAAGT | GGTTCTTTTA | GAAGGGTGGT | TGGTGTTGGC | ACATACTCCA | AGCACTCAGG | 2940 |
| TTTTGAGTTT | GTCCCAGGAA | TGAAGACTGC | ATTACTGCCG | CCCCTCCCTG | GTAAGGGCTA | 3000 |
| CACAGAGAAA | TCCTATTTGG | AGCCTATCCT | GGTAACTCGC | TCTGTAGACC | AGGCTGGCCT | 3060 |
| CGAACTCAAG | AGAACCACCT | GCCTCTGAAT | GCTGGTATTA | AGGGCAGGCA | CCACCAACAC | 3120 |
| CCAGCCTAAA | AAATGTCTTT | TTTTTAAAGA | TTTTTTTTTT | TTTTTTACA | GAATAAACAT | 3180 |
| TCTGTTTACA | ATATTCTGCT | TCTATGTATA | TCTGCACACT | AGAAGAGGGC | ACCCGATCTC | 3240 |
| ATAATGGATG | GTTGTGAGCC | ACCAAGTGGT | TGCTGGGAAT | TGAACTCAGA | ACCTCTGGAA | 3300 |
| GAGCAGTCAG | TGCTCTTAAC | CTCTGAGCCA | TCTCTCCAGC | CCCTAAAAAT | GGCTCTTGAG | 3360 |
| ATAGGGTCTC | AAGTAGTTTG | AGACTGAGTT | GGCTATATAA | ACAAGGCTGG | CACATAGCAC | 3420 |
| CATGTACAGC | TGGGTTTAGT | TTACATGGGG | TGTTTTTGTC | TCTGGAGGCA | GGAGGATCAT | 3480 |
| TTGAGCATAG | GGAGTTAATA | GTGAGGTCAT | GTTTTATCTA | CTCTTCTGAA | TTGAGAACTA | 3540 |
| AGCTGATGCA | AAGCAAGTTT | GACTGAAGAA | GTCCAGTTTA | TGAGAACAAG | GGTGGAAACT | 3600 |
| AATGTGTCAA | AGATGGCCTT | GCATGTGTTT | TAGATGATGA | CCCAGTCACT | TGGGAATTAC | 3660 |

| | | | | | | |
|---|---|---|---|---|---|---|
| TGGATGTGTA | AGACCTATAT | CTTGACAGGA | GTGAACAGTG | TCTTATAGGT | CCTATATGAA | 3720 |
| AGAAATGAGA | CATACCCATT | TTGTTTCCCC | TAAGAATTCA | CTTTTCCTAA | CCTGGTTCAT | 3780 |
| GCTATTTAGG | TTATTTTACT | TGCAAATCCT | AGGTGCTCCC | TTACCCAGTA | TTGCTTATGT | 3840 |
| GGCACCAAAG | TCACTCACTC | CCATGATTTG | CAAGTCTCTG | GAACTTCCA | TGACAACCTA | 3900 |
| GAATAGCAAC | TCAAATACAT | TTTCTCAGTA | CCAATTTTGA | AGAAAAAATA | TTTTGCAAAA | 3960 |
| TAGCTGTATG | GATGGGTACT | AAATAGTGAG | GTTATCTCCA | GAAGGCCTAT | GAAGAATTAA | 4020 |
| GGTTGAGTTC | AGTTGAGTTC | AGCAGCAAGT | TTAAGGTTCA | TCCATTTTTG | TACAGTGTTT | 4080 |
| TCCTATTACG | GTAAGTGTTT | TGCCTGCAGG | AATATCTGTA | CCACATGCTT | GCCTGGTACC | 4140 |
| TATATCGGCC | AGAAGAGGGC | TTTGGATCCT | CTGGACTTGA | ATTACAGATG | GGTATTAGCC | 4200 |
| ACCATTTAGG | TGCTGGGAAT | TGAAACCAAG | TCCTCTGGAA | GAACAGCAAG | TGATCGAGTC | 4260 |
| GAC | | | | | | 4263 |

( 2 ) INFORMATION FOR SEQ ID NO:29:

( i ) SEQUENCE CHARACTERISTICS:
        ( A ) LENGTH: 4695 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

| | | | | | | |
|---|---|---|---|---|---|---|
| CCCGGGCTGG | GCTGAGACCC | GCAGAGGAAG | ACGCTCTAGG | GATTTGTCCC | GGACTAGCGA | 60 |
| GATGGCAAGG | CTGAGGACGG | GAGGCTGATT | GAGAGGCGAA | GGTACACCCT | AATCTCAATA | 120 |
| CAACCTTTGG | AGCTAAGCCA | GCAATGGTAG | AGGGAAGATT | CTGCACGTCC | CTTCCAGGCG | 180 |
| GCCTCCCCGT | CACCACCCCC | CCCAACCCGC | CCCGACCGGA | GCTGAGAGTA | ATTCATACAA | 240 |
| AAGGACTCGC | CCCTGCCTTG | GGAATCCCA | GGACCGTCG | TTAAACTCCC | ACTAACGTAG | 300 |
| AACCCAGAGA | TCGCTGCGTT | CCCGCCCCCT | CACCCGCCCG | CTCTCGTCAT | CACTGAGGTG | 360 |
| GAGAAGAGCA | TGCGTGAGGC | TCCGGTGCCC | GTCAGTGGGC | AGAGCGCACA | TCGCCCACAG | 420 |
| TCCCCGAGAA | GTTGGGGGGA | GGGGTCGGCA | ATTGAACCGG | TGCCTAGAGA | AGGTGGCGCG | 480 |
| GGGTAAACTG | GGAAAGTGAT | GTCGTGTACT | GGCTCCGCCT | TTTTCCCGAG | GGTGGGGGAG | 540 |
| AACCGTATAT | AAGTGCAGTA | GTCGCCGTGA | ACGTTCTTTT | TCGCAACGGG | TTTGCCGCCA | 600 |
| GAACACAGGT | AAGTGCCGTG | TGTGGTTCCC | GCGGGCCTGG | CCTCTTACG | GGTTATGGCC | 660 |
| CTTGCGTGCC | TTGAATTACT | TCCACGCCCC | TGGCTGCAGT | ACGTGATTCT | TGATCCCGAG | 720 |
| CTTCGGGTTG | GAAGTGGGTG | GGAGAGTTCG | AGGCCTTGCG | CTTAAGGAGC | CCCTTCGCCT | 780 |
| CGTGCTTGAG | TTGAGGCCTG | GCCTGGGCGC | TGGGGCCGCC | GCGTGCGAAT | CTGGTGGCAC | 840 |
| CTTCGCGCCT | GTCTCGCTGC | TTTCGATAAG | TCTCTAGCCA | TTTAAAATTT | TTGATGACCT | 900 |
| GCTGCGACGC | TTTTTTTCTG | GCAAGATAGT | CTTGTAAATG | CGGGCCAAGA | TCTGCACACT | 960 |
| GGTATTTCGG | TTTTTGGGGC | CGCGGGCGGC | GACGGGGCCC | GTGCGTCCCA | GCGCACATGT | 1020 |
| TCGGCGAGGC | GGGGCCTGCG | AGCGCGGCCA | CCGAGAATCG | GACGGGGTA | GTCTCAAGCT | 1080 |
| GGCCGGCCTG | CTCTGGTGCC | TGGCCTCGCG | CCGCCGTGTA | TCGCCCCGCC | CTGGGCGGCA | 1140 |
| AGGCTGGCCC | GGTCGGCACC | AGTTGCGTGA | GCGGAAAGAT | GGCCGCTTCC | CGGCCCTGCT | 1200 |
| GCAGGGAGCT | CAAAATGGAG | GACGCGGCGC | TCGGGAGAGC | GGGCGGGTGA | GTCACCCACA | 1260 |
| CAAAGGAAAA | GGGCCTTTCC | GTCCTCAGCC | GTCGCTTCAT | GTGACTCCAC | GGAGTACCGG | 1320 |
| GCGCCGTCCA | GGCACCTCGA | TTAGTTCTCG | AGCTTTTGGA | GTACGTCGTC | TTTAGGTTGG | 1380 |

-continued

| | | | | | |
|---|---|---|---|---|---|
| GGGGAGGGGT | TTTATGCGAT | GGAGTTTCCC | CACACTGAGT | GGGTGGAGAC | TGAAGTTAGG | 1440 |
| CCAGCTTGGC | ACTTGATGTA | ATTCTCCTTG | GAATTTGCCC | TTTTTGAGTT | TGGATCTTGG | 1500 |
| TTCATTCTCA | AGCCTCAGAC | AGTGGTTCAA | AGTTTTTTC | TTCCATTTCA | GGTGTCGTGA | 1560 |
| AAACTACCCC | TAAAAGCCAA | AATGGGAAAG | GAAAAGACTC | ATATCAACAT | TGTCGTCATT | 1620 |
| GGACACGTAG | ATTCGGGCAA | GTCCACCACT | ACTGGCCATC | TGATCTATAA | ATGCGGTGGC | 1680 |
| ATCGACAAAA | GAACCATTGA | AAAATTTGAG | AAGGAGGCTG | CTGAGGTATG | TTTAATACCA | 1740 |
| GAAAGGGAAA | GATCAACTAA | AATGAGTTTT | ACCAGCAGAA | TCATTAGGTG | ATTTCCCCAG | 1800 |
| AACTAGTGAG | TGGTTTAGAT | CTGAATGCTA | ATAGTTAAGA | CCTTACTTAT | GAAATAATTT | 1860 |
| TGCTTTTGGT | GACTTCTGTA | ATCGTATTGC | TAGTGAGTAG | ATTTGGATGT | TAATAGTTAA | 1920 |
| GATCCTACTT | ATAAAAGTTT | GATTTTGGT | TGCTTCTGTA | ACCCAAAGTG | ACCAAAATCA | 1980 |
| CTTTGGACTT | GGAGTTGTAA | AGTGGAAACT | GCCAATTAAG | GGCTGGGGAC | AAGGAAATTG | 2040 |
| AAGCTGGAGT | TTGTGTTTTA | GTAACCAAGT | AACGACTCTT | AATCCTTACA | GATGGGAAAG | 2100 |
| GGCTCCTTCA | AGTATGCCTG | GGTCTTGGAT | AAACTGAAAG | CTGAGCGTGA | ACGTGGTATC | 2160 |
| ACCATTGATA | TCTCCTTGTG | GAAATTTGAG | ACCAGCAAGT | ACTATGTGAC | TATCATTGAT | 2220 |
| GCCCCAGGAC | ACAGAGACTT | TATCAAAAC | ATGATTACAG | GACATCTCA | GGTTGGGATT | 2280 |
| AATAATTCTA | GGTTTCTTTA | TCCCAAAAGG | CTTGCTTTGT | ACACTGGTTT | TGTCATTTGG | 2340 |
| AGAGTTGACA | GGGATATGTC | TTTGCTTTCT | TTAAAGGCTG | ACTGTGCTGT | CCTGATTGTT | 2400 |
| GCTGCTGGTG | TTGGTGAATT | TGAAGCTGGT | ATCTCCAAGA | ATGGGCAGAC | CCGAGAGCAT | 2460 |
| GCCCTTCTGG | CTTACACACT | GGGTGTGAAA | CAACTAATTG | TCGGTGTTAA | CAAAATGGAT | 2520 |
| TCCACTGAGC | CACCCTACAG | CCAGAAGAGA | TATGAGGAAA | TTGTTAAGGA | AGTCAGCACT | 2580 |
| TACATTAAGA | AAATTGGCTA | CAACCCCGAC | ACAGTAGCAT | TTGTGCCAAT | TTCTGGTTGG | 2640 |
| AATGGTGACA | ACATGCTGGA | GCCAAGTGCT | AACGTAAGTG | GCTTTCAAGA | CCATTGTTAA | 2700 |
| AAAGCTCTGG | GAATGGCGAT | TTCATGCTTA | CACAAATTGG | CATGCTTGTG | TTTCAGATGC | 2760 |
| CTTGGTTCAA | GGGATGGAAA | GTCACCCGTA | AGGATGGCAA | TGCCAGTGGA | ACCACGCTGC | 2820 |
| TTGAGGCTCT | GGACTGCATC | CTACCACCAA | CTCGTCCAAC | TGACAAGCCC | TTGCGCCTGC | 2880 |
| CTCTCCAGGA | TGTCTACAAA | ATTGGTGGTA | AGTTGGCTGT | AAACAAAGTT | GAATTTGAGT | 2940 |
| TGATAGAGTA | CTGTCTGCCT | TCATAGGTAT | TTAGTATGCT | GTAAATATTT | TTAGGTATTG | 3000 |
| GTACTGTTCC | TGTTGGCCGA | GTGGAGACTG | GTGTTCTCAA | ACCCGGTATG | GTGGTCACCT | 3060 |
| TTGCTCCAGT | CAACGTTACA | ACGGAAGTAA | AATCTGTCGA | AATGCACCAT | GAAGCTTTGA | 3120 |
| GTGAAGCTCT | TCCTGGGGAC | AATGTGGGCT | TCAATGTCAA | GAATGTGTCT | GTCAAGGATG | 3180 |
| TTCGTCGTGG | CAACGTTGCT | GGTGACAGCA | AAAATGACCC | ACCAATGGAA | GCAGCTGGCT | 3240 |
| TCACTGCTCA | GGTAACAATT | TAAAGTAACA | TTAACTTATT | GCAGAGGCTA | AAGTCATTTG | 3300 |
| AGACTTTGGA | TTTGCACTGA | ATGCAAATCT | TTTTTCCAAG | GTGATTATCC | TGAACCATCC | 3360 |
| AGGCCAAATA | AGCGCCGGCT | ATGCCCTGT | ATTGGATTGC | CACACGGCTC | ACATTGCATG | 3420 |
| CAAGTTTGCT | GAGCTGAAGG | AAAAGATTGA | TCGCCGTTCT | GGTAAAAAGC | TGGAAGATGG | 3480 |
| CCCTAAATTC | TTGAAGTCTG | GTGATGCTGC | CATTGTTGAT | ATGGTTCCTG | GCAAGCCCAT | 3540 |
| GTGTGTTGAG | AGCTTCTCAG | ACTATCCACC | TTTGGGTAAG | GATGACTACT | TAAATGTAAA | 3600 |
| AAAGTTGTGT | TAAAGATGAA | AAATACAACT | GAACAGTACT | TTGGGTAATA | ATTAACTTTT | 3660 |
| TTTTTAATAG | GTCGCTTTGC | TGTTCGTGAT | ATGAGACAGA | CAGTTGCGGT | GGGTGTCATC | 3720 |
| AAAGCAGTGG | ACAAGAAGGC | TGCTGGAGCT | GGCAAGGTCA | CCAAGTCTGC | CCAGAAAGCT | 3780 |

-continued

| | | | | | | |
|---|---|---|---|---|---|---|
| CAGAAGGCTA | AATGAATATT | ATCCCTAATA | CCTGCCACCC | CACTCTTAAT | CAGTGGTGGA | 3840 |
| AGAACGGTCT | CAGAACTGTT | TGTTTCAATT | GGCCATTTAA | GTTAGTAGT | AAAAGACTGG | 3900 |
| TTAATGATAA | CAATGCATCG | TAAAACCTTC | AGAAGGAAAG | GAGAATGTTT | TGTGGACCAC | 3960 |
| TTTGGTTTTC | TTTTTTGCGT | GTGGCAGTTT | TAAGTTATTA | GTTTTTAAAA | TCAGTACTTT | 4020 |
| TTAATGGAAA | CAACTTGACC | AAAAATTTGT | CACAGAATTT | TGAGACCCAT | TAAAAAAGTT | 4080 |
| AAATGAGAAA | CCTGTGTGTT | CCTTTGGTCA | ACACCGAGAC | ATTTAGGTGA | AAGACATCTA | 4140 |
| ATTCTGGTTT | TACGAATCTG | GAAACTTCTT | GAAATGTAA | TTCTTGAGTT | AACACTTCTG | 4200 |
| GGTGGAGAAT | AGGGTTGTTT | TCCCCCCACA | TAATTGGAAG | GGGAAGGAAT | ATCATTTAAA | 4260 |
| GCTATGGGAG | GGTTTCTTTG | ATTACAACAC | TGGAGAGAAA | TGCAGCATGT | TGCTGATTGC | 4320 |
| CTGTCACTAA | AACAGGCCAA | AAACTGAGTC | CTTGGGTTGC | ATAGAAAGCT | TCATGTTGCT | 4380 |
| AAACCAATGT | TAAGTGAATC | TTTGGAAACA | AAATGTTTCC | AAATTACTGG | GATGTGCATG | 4440 |
| TTGAAACGTG | GGTTAAAATG | ACTGGGCAGT | GAAAGTTGAC | TATTTGCCAT | GACATAAGAA | 4500 |
| ATAAGTGTAG | TGGCTAGTGT | ACACCCTATG | AGTGGAAGGG | TCCATTTTGA | AGTCAGTGGA | 4560 |
| GTAAGCTTTA | TGCCATTTTG | ATGGTTTCAC | AAGTTCTATT | GAGTGCTATT | CAGAATAGGA | 4620 |
| ACAAGGTTCT | AATAGAAAAA | GATGGCAATT | TGAAGTAGCT | ATAAAATTAG | ACTAATTACA | 4680 |
| TTGCTTTTCT | CCGAC | | | | | 4695 |

HAMSTER EF-1α TRANSCRIPTIONAL REGULATORY DNA

BACKGROUND OF THE INVENTION

Transcription of any given eukaryotic gene is carried out by one of three RNA polymerase enzymes each of which acts on a particular subset of genes. While transcription of large ribosomal RNAs is performed by RNA polymerase I and small ribosomal RNA and tRNA is transcribed by RNA polymerase III, protein-coding DNA sequences and most small nuclear RNAs are transcribed by RNA polymerase II. For each type of gene, transcription requires interaction of the appropriate polymerase with the gene's promoter sequences and formation of a stable transcription initiation complex. In general, transcription from any of the three polymerases also requires interaction of some binding factor with the promoter sequence and recognition of the binding factor by a second factor which thereby permits polymerase interaction with the gene sequence. While this mechanism is the minimum requirement for transcription with RNA polymerases I and III, the process leading to transcription with RNA polymerase II is more intricate.

Presumably due to the vast array of gene sequences transcribed by RNA polymerase II and the fact that the regulation patterns for these genes are highly variable within the same cell and from cell to cell, transcription by RNA polymerase II is affected by binding of numerous transcription factors in the initiation complex in addition to the interactions of other binding proteins to regulatory DNA sequences other than the promoter. These other binding proteins can serve to activate transcription beyond a basal level or repress transcription altogether. Repressor binding can also be viewed as a means to prevent activation in view of observations that basal transcriptional in higher eukaryotes is normally very low. Activation, on the other hand, is ordinarily the end response to some physiological signal and requires either removal of repressor binding proteins or alteration in chromatin structure in order to permit formation of an active transcription initiation complex.

At the core of transcription complex formation, and a prerequisite for basal levels of gene expression, is the promoter sequence called the "TATA" box which is located upstream from the polymerase II transcription start site. The TATA box is the binding site for a ubiquitous transcription factor designated TFIID, but as mentioned, transcription from the promoter sequence in most genes is strongly influenced by additional regulatory DNA sequences which can either enhance or repress gene transcription. DNA elements of this type are in variable positions with respect to coding sequences in a gene and with respect to the TATA box. These additional transcriptional regulatory elements often function in a tissue- or cell-specific manner.

In expression of recombinant proteins, it is particularly important to select regulatory DNA which includes the promoter TATA sequence and additional regulatory elements compatible with the host cell's transcriptional machinery. For this reason, regulatory DNA endogenous to the host cell of choice is generally preferred. Alternatively, considerable success has been achieved using regulatory DNA derived from viral genomic sequences in view of the broad host range of viruses in general and the demonstrated activity of viral regulatory DNA in different cell types. Well known and routinely utilized viral regulatory DNAs for recombinant protein expression include, for example, the SV40 early gene promoter/enhancer [Dijkema, et al., *EMBO J.* 4:761 (1985)], Rous sarcoma virus long terminal repeat DNA [Gorman, et al., *Proc. Natl. Acad. Sci. (USA)* 79:6777 (1982b)], bovine papillomavirus fragments [Sarver, et al., *Mo. Cell. Biol.* 1:486 (1981)] and human cytomegalovirus promoter/enhancer elements [Boshart et al., *Cell* 41:521 (1985)]. Despite the broad range of cell types in which viral regulatory DNAs have been demonstrated to be functional, it is possible that non-viral promoter/enhancer DNA elements exist which permit elevated transcription of recombinant proteins in specific cell lines through more efficient use of host cell transcriptional machinery.

Thus there exists a need in the art to identify promoter/enhancer regulatory DNA sequences which function in homologous and heterologous cell types to increase recombinant protein expression and provide a high yield of a desired protein product. Of particular importance is the need to identify such promoter/enhancer regulatory DNA which can be utilized most efficiently in mammalian cells in order to increase production of recombinant proteins in vitro which are glycosylated in a manner akin to glycosylation patterns which result from in vivo protein expression. Proteins expressed in this manner and administered therapeutically or prophylactically are less likely to be antigenic and more likely to be physiologically active. Regulatory DNA sequences of this type are also amenable to being inserted into host cells in order to increase expression of genes endogenous to the host cells or genes previously introduced into the genome of the host cell by techniques well known and routinely practiced in the art.

SUMMARY OF THE INVENTION

The present invention relates to purified and isolated polynucleotides derived from hamster cells which regulate gene transcription. The polynucleotides comprise regulatory DNA sequences 5' to translated regions of the Chinese hamster ovary EF-1α gene. Preferred DNA of the invention is designated the CHEF1 regulatory DNA and includes approximately 3.7 kb DNA extending from a SpeI restriction site to the initiating methionine (ATG) codon of the EF-1α protein. Polynucleotides of less than 3.7 kb are also comprehended by the invention in as much as the smaller fragment polynucleotides are capable of increasing transcription of an operatively linked gene. Active fragments of the DNAs of the invention, defined by the capacity to regulate (i.e., enhance) gene transcription, are readily identifiable through deletion studies well known and routinely practiced in the art. Regulatory DNA of the invention includes polynucleotides isolated from natural sources, such as cultured cells, as well as polynucleotides produced by enzymatic or purely chemical synthesis. Thus, in one embodiment, the invention provides a method for preparing CHEF1 DNA from a genomic library. Alternatively, the DNA may be constructed by enzymatic synthesis, utilizing, for example, the polymerase chain reaction (PCR), or purely chemical synthesis wherein single nucleotides are successively added or overlapping oligonucleotides are hybridized and ligated. The DNA sequence of the most preferred embodiment is set out in SEQ ID NO: 1. The invention further embraces DNA sequences which hybridize under stringent conditions to DNA set out in SEQ ID NO: 1. Stringent conditions include washing at about 65° C. in buffer containing about 2× SSC and about 0.1% SDS or equivalent conditions.

The invention further comprehends plasmid DNA comprising CHEF1 regulatory polynucleotides. Plasmids of the invention may also include DNA sequences encoding a protein of interest or RNA product of interest operatively linked to the CHEF1 polynucleotide sequences. The invention further comprehends host cells transformed, transfected, and or electroporated with polynucleotides or plasmids of the invention. Plasmid DNA of the invention may be integrated into the genome of the host cell or may exist in the cell in closed circular plasmid form. Preferred plasmids of the invention particularly amenable for insertion of desired DNA sequences include plasmids pDEF14 and pDEF2. Bacterial host cells transformed with pDEF14 and pDEF2 were deposited on Apr. 9, 1997, and Mar. 4, 1997, respectively, with the American Type Culture Collection, 10801 University Boulevard, Manassas, Va. 20110-2209 and assigned Accession Numbers 98389 and 98343, respectively.

The invention also comprehends linear vector DNA comprising CHEF1 polynucleotides. Vectors of the invention may be obtained from viral sources or may be synthesized in vitro. The invention further comprehends host cells transfected or electroporated with the linear vector sequences. DNA of this type is particularly useful for expression of heterologous gene sequences operatively linked to the CHEF1 DNA sequences, or for site directed homologous recombination wherein CHEF1 sequences can be inserted into the genome of a host cell in order to modulate expression of an operatively linked sequence.

The invention further provides chimeric recombinant DNA molecules wherein the CHEF1 DNA is operably linked to (i.e., promotes transcription of) gene sequences encoding a desired protein product. Chimeric molecules in general are those comprising domains not normally found in association in a wild-type environnment; in the present invention, a chimeric DNA can comprise part or all of the CHEF1 regulatory DNA in association with a DNA sequence other than the gene encoding hamster EF-1α protein. Protein products encoded by the chimeric molecules include physiologically active proteins, portions or subunits of active proteins, as well as marker, or reporter, proteins. The polynucleotide sequence encoding the protein product may be derived from complementary DNA (cDNA), genomic DNA, synthetic DNA, or DNA derived from combinations of molecules of these types. Protein products may be endogenous (i.e., normally found in the CHO genome absent introduction of DNA by transformation, transfection, or the like) to Chinese hamster ovary (CHO) cells. In addition, protein products may be encoded by exogenous sources, an exogenous source being one other than the genome of a CHO cell, including, for example, a synthesized DNA. Preferred chimeric molecules of the invention include those wherein CHEF1 DNA is operatively linked to DNA encoding: (i) the heavy chain of anti-ICAM3 antibody ICM3, (ii) the light chain of ICM3, (iii) the heavy chain of anti-CD11/CD18 antibody hu23F2G, (iv) the light chain of hu23F2G, (v) chitinase, (vi) platelet activating factor acetyl hydrolase (PAF-AH), and (vii) macrophage derived chemokine (MDC). Bacterial host cells transformed with plasmid DNA comprising the chimeric molecules were deposited on Apr. 1, 1997 with the American Type Culture Collection and assigned Accession Numbers (i) 98381, (ii) 98382, (iii) 98383, (iv) 98384, (v) 98385, (vi) 98386, and (vii) 98387, respectively.

The invention further relates to host cells transformed or transfected with the CHEF1 DNAs of the invention. Preferred host cells of the invention are derived from Chinese hamsters (*Cricetulus griseus*) in which the CHEF1 regulatory DNA would be expected to provide high levels of protein expression. The invention, however, embraces other cell types derived from alternative species, including, for example, from Armenian hamsters (*Cricetulus migratoris*) or Syrian (golden) hamsters (*Mesocricetus auratus*), as well as cell types derived from animals of other genera. Cells can be obtained from lung, ovary, peritoneum, muscle, pancreas, kidney, melanoma, or somatic sources, as well as from whole fetus or whole embryo. Host cells of the invention listed above, as well as other cell types, for example, myeloma cell lines, in which the CHEF1 regulatory DNA would be expected to provide high levels of transcription, can be obtained from the American Type Culture Collection or alternatively, cultured directly from animal sources.

Recombinant molecules of the invention which include CHEF1 regulatory DNA will provide for increased levels of mRNA expression of the operably linked heterologous (i.e., not normally found in the host genome absent introduction of polynucleotides by tranfection, transformation, or the like) polynucleotides. Depending on the nature of the polynucleotide linked to the CHEF1 polynucleotide sequences, increased transcription would ultimately result in elevated levels of polypeptides, or increased levels of various RNA species in those instances wherein the linked polynucleotide encodes, for example, transfer RNA, ribosomal RNA, small nuclear RNA and the like. RNA species may also include anti-sense RNA complementary to mRNA transcribed from an endogenous or exogenous gene sequence. Increased polypeptide translation would necessarily depend on the presence of appropriate translation signals being present in the mRNA.

The invention further provides methods by which the CHEF1 DNA is inserted into specific sites in genomic DNA of host cells in order to increase transcription levels of an endogenous gene sequence. Homologous recombination can be utilized to insert all or part of the CHEF1 DNA. In host cells modified in this manner, CHEF1 DNA is operably linked to coding DNA sequences. See, for example, PCT International Publication No. WO 94/12650; PCT International Publication No. WO 92/20808; and PCT International Publication No. WO 91/09955. Necessarily, the invention embraces altered genomic DNA sequences wherein the CHEF1 regulatory DNA has been inserted.

Alternatively, the invention embraces host cells wherein exogenous DNA is inserted adjacent and in an operative position with respect to CHEF1 DNA present in the genome. Host cells of this type include CHO cells and the inserted sequence either replaces EF-1α coding DNA or is inserted between CHEF1 regulatory DNA and EF-1α coding DNA. The invention also embraces host cells other than CHO cells wherein CHEF1 DNA has previously been inserted into the genome and additional DNA is subsequently inserted into an operatively linked position.

The invention further provides methods for increasing transcription of a desired gene comprising the step of introducing into a host cell a polynucleotide comprising a hamster EF-1α regulatory sequence in such a manner that the regulatory sequence integrates into the genomic DNA of the host in an operatively linked position with respect to the desired gene. The invention further comprehends a method for increasing transcription of a desired gene comprising the step of introducing into a host cell a polynucleotide comprising a hamster EF-1α regulatory sequence and a targeting sequence, said targeting sequence constructed in a manner which permits integration of the regulatory sequences at a position operatively linked to the desired gene encoding a protein other than EF-1α. The methods of the invention include means to increase transcription of genes endogenous to CHO cells as well as means to increase transcription of genes exogenous to CHO cells.

Recombinant molecules of the invention may be used for the production of transgenic animals wherein chimeric recombinant DNA including CHEF1 DNA operably linked to a DNA sequence of interest is introduced into developing germ or somatic cells of an animal. Chimeric recombinant molecules may be introduced for example by microinjection, and when carried out using germ cells, cells in the resulting animal may all include the recombinant DNA of the invention. Alternatively, chimeric recombinant DNA of the invention may be introduced into cells of an embryo and a plurality of cells in the resulting animal may include DNA of the invention.

CHEF1 DNA is also useful for identification of closely related regulatory DNA sequences which may impart increased gene expression over and beyond that which CHEF1 permits. Similarly, knowledge of CHEF1 DNA sequences permits construction of synthetic DNAs, either from de novo synthesis or single or multiple modifications of CHEF1 sequences, the resulting synthetic DNAs having sequences similar to CHEF1 but capable of promoting higher levels of gene transcription.

DETAILED DESCRIPTION OF THE INVENTION

The present invention is illustrated by the following examples. Example 1 describes cloning of the hamster EF-1α gene and the cognate CHEF1 regulatory DNA. Example 2 relates to subcloning and sequence analysis of the CHEF1 regulatory sequence. Example 3 provides characterization of the CHEF1 promotor polynucleotide, and Example 4 provides a description of how various expression vectors were constructed which included CHEF1 DNA. Example 5 describes transfection assays utilized to determine the efficiency of the CHEF1 regulatory DNA. Example 6 details a comparison of recombinant protein expression levels using either the CHEF1 regulatory DNA or the cytomegalovirus (CMV) promoter. Example 7 examines differences in regulatory capacity of CHEF1 DNA of different lengths.

EXAMPLE 1

Cloning of CHEF1

A Chinese hamster ovary genomic DNA library (CHO-K1) (Stratagene, La Jolla, Calif.) was screened with cDNA encoding human EF-1α in an attempt to isolate a hamster homolog to the human EF-1α gene.

The CHO-K1 library, a partial Sau3A digest in Lambda FIX®II cloning vector, was obtained from Stratagene (La Jolla, Calif.) in host cell strains XL-1-Blue MRA and XL1-Blue MRA (P2). The host cells were prepared according to the manufacturer's suggested protocol with the following modifications.

Briefly, cells from glycerol stocks were streaked on LB plates containing no antibiotic. Single colonies were selected for inoculating liquid LB media and grown to late log phase and an $OD_{600}$ of approximately 0.9. At this point, cells were either stored according to manufacturer's suggested protocol or used immediately as described below.

In preparation of cultures for plating, single colonies picked from plates prepared as described above were used for inoculation and cells were grown in 50 ml LB medium supplemented with 0.5 ml 1M $MgSO_4$ and 1 ml 10% maltose in deionized water. Following overnight growth at 30° C., cells were harvested by centrifugation in a tabletop centrifuge (2000 rpm for 5 minutes at room temperature) and resuspended in 10 mM $MgSO_4$ at an $OD_{600}$ of 0.5

Lambda phage, supplied by the manufacturer, was diluted in SM buffer (prepared to 1 liter stock containing 5.8 g NaCl, 2.0 g $MgSO_4.H_2O$, 50 ml 1M Tris-HCl, pH 7.5, and 5 ml 2% [w/v] gelatin) over a range of 10- to $10^5$-fold, and 2 μl of each dilution was added to 400 μl host cells in 10 mM $MgSO_4$ ($OD_{600}$≈0.5). The resulting mixture was incubated for 15 minutes at 37° C. to allow attachment of phage to the cells, top agar (0.75% LBM agarose at 48° C.) was added, and each mixture plated in duplicate on LBM agarose plates. Results indicated a titer of $3\times10^6$ plaque forming units (pfu)/μl phage stock.

Fresh host cells were prepared as described above prior to screening of the library. Approximately 50,000 phage pfu were added to 600 μl host cells (at $OD_{600}$≈0.5) with 6.5 ml 0.75% LBM agarose at 48° C. The mixture was spread onto agarose plates which were then incubated for approximately 8 hours at 37° C. The plates were subsequently cooled for 5 hours at 4° C. to prevent top agarose from sticking to nitrocellulose overlays. Membranes, BA-85, 0.45 μm pore size, (S+S, Keene, N.H.) were placed over the plates and transfer continued for two minutes. Membranes were removed from the plates and the transferred DNA denatured in 1.5M NaCl/0.5M NaOH for two minutes. Filters were neutralized for 5 minutes in 1.5M NaCl/1.0M Tris-HCl (pH 8.0), blotted on Whatman 3-MM paper, and baked under vacuum at 80° C. for approximately 1.5 to 2 hours.

A human EF-1α cDNA sequence [Uetsuki, et al. *J. Biol. Chem.* 264:5791–5798 (1989)], previously shown to be 95% identical to the coding region of CHO EF-1α [Hayashi, et al. *J. Biochem.* 106:560–563 1989], was used as probe for library screening and prepared as described below. The 1.4 kb human EF-1α probe was derived from plasmid M0107, a pRc/CMV (Invitrogen, San Diego, Calif.) vector containing human EF-1α cDNA inserted at an EcoRI site. In order to first confirm that plasmid M0107 contained the expected human cDNA, insert DNA was sequenced with 3' and 5' vector primers.

94-17 AGGCACAGTCGAGGCTGATC (SEQ ID NO: 2)

94-18 TTCCAGGGTCAAGGAAGGCA (SEQ ID NO: 3)

The first 263 bp of the insert showed greater than 90% identity with the published human EF-1α coding sequence, and while the sequence in the 3' end was difficult to accurately determine, small stretches could be aligned with the expected sequence. Combined, these alignments indicated the plasmid encoded the desired sequence.

The entire human insert was removed from the plasmid with EcoRI digestion and a cDNA band of 1.4 kb was gel purified twice using QIAGEN QIAquick Gel Extraction Kit according to the manufacturer's suggested protocol. The DNA was eluted into 50 μl TE, the resulting solution concentrated in a Microcon-10 (Amicon, Beverly, Mass.) to 25 μl, and an aliquot labeled with $^{32}$P-α-dTTP and $^{32}$P-α-dCTP using a Boehringer Mannheim Random Primed DNA labelling kit according to the manufacturer's suggested protocol. Labeled probe was purified using a G50 spin column to remove unincorporated nucleotides and comparison of purified probe to the pre-spin aliquot showed 46% incorporation of the radioactive label, with counts of $5\times10^5$ cpm/min/μl.

The nitrocellulose membranes prepared as described above were probed as follows. A stock pre-hybridization/hybridization buffer solution was prepared which included 22.5 ml 20× SSC, 30.0 ml 50× Denhardt's solution, 3.0 ml 1M phosphate buffer (pH 6.8) (69 ml 1M $NaH_2HPO_4$, 31 ml 1M $Na_2HPO_4$), 0.75 ml 20% SDS, and 78.75 ml $dH_2O$. For pre-hybridization, 1.4 ml 10 mg/ml salmon sperm DNA (Stratagene) was boiled 5 minutes with 0.6 ml $dH_2O$, then added to 7 ml $dH_2O$ and 72 ml stock buffer solution. Filters were incubated at 65° C. for a minimum of two hours in pre-hybridization buffer.

For hybridization, 30 µl probe, 200 µl 10 mg/ml salmon sperm DNA and 770 µl dH$_2$O were combined, boiled for 5 minutes, and added to 36 ml stock buffer with 3 ml dH$_2$O. The pre-hybridization solution was removed from the filters, hybridization buffer added and the filters incubated at 65° C. overnight. Following hybridization, filters were washed for three hours at 65° C. with three changes of buffer containing 2× SSC and 0.1% SDS, and then autoradiographed for 48 hours.

Forty-seven positive colonies were identified and picked into 1 ml SM buffer containing 20 µl chloroform. In order to weed out possible pseudogenes missing one or more introns, PCR primer pairs were designed to flank two introns each: primers 95-136 (SEQ ID NO: 4) and 95-137 (SEQ ID NO: 5) spanning introns 2 and 3; primers 95-138 (SEQ ID NO: 6) and 95-139 (SEQ ID NO: 7) spanning introns 3 and 4; primers 95-140 (SEQ ID NO: 8) and 95-141 (SEQ ID NO: 9) spanning introns 4 and 5; and primers 95-142 (SEQ ID NO: 10) and 95-143 (SEQ ID NO: 11) spanning introns 6 and 7.

95-136 (SEQ ID NO: 4) GCCACCTGATCTACAAATGT
95-137 (SEQ ID NO: 5) GAGATACCAGCCT-CAAATTC
95-138 (SEQ ID NO: 6) ATGTGACCATCATTGATGCC
95-140 (SEQ ID NO: 8) GTTGGAATGGTGACAA-CATG
95-141 (SEQ ID NO: 9) CAGGTTTTAAAACAC-CAGTC
95-142 (SEQ ID NO: 10) AATGACCCACCAATG-GAAGC
95-143 (SEQ ID NO: 11) ACAGCAACTGTCTGCCT-CAT

Predicted size of PCR products using CHO EF-1α template DNA was based on size and location of introns in the published human EF-1α sequence. Each PCR reaction included 2 µl phage, 2.5 µl each primer of the appropriate pair (100 µg/ml), 2 µl 2 mM dNTP mix, 2.5 µl 10× PCR buffer (Roche Molecular Systems, Branchburg, N.J.), 1.5 µl 25 mM MgCl$_2$, 0.125 µl Taq polymerase (5 units/µl) (Perkin Elmer) and 11.8 µl dH$_2$O. Amplification was carried out for 4 minutes at 94° C., followed by 30 cycles of 1 minute at 90° C., 2 minutes at 50° C., and 4 minutes at 72° C. Amplification products were separated on 1.2% agarose gels run in 1× TAE.

Three of the 47 positive plaques were found to encode true genes (#2, 7 and 40) containing all introns and the three positive samples were subjected to tertiary screening as follows. Plating cultures were prepared as described above with 10 to 10$^5$ dilution of stocks prepared for each of the three positive plaques. Twenty to fifty isolated plaques from each stock were screened by PCR with the following results. Clone #2 yielded two positives (designated 2.12 and 2.17) from twenty screened, clone #7 yielded one (designated 7.44) in fifty screened, and clone #40 yielded one positive (designated positive 40.24) in forty screened. Phage DNA was isolated from each of the four samples as follows.

XL-1 Blue MRA (P2) host cells were streaked out on LB agarose plates and grown overnight at 37° C. A single colony was selected to inoculate 50 ml of LB media (containing 0.2% maltose and 10 mM MgSO$_4$) and the culture grown overnight at 30° C. Cells were harvested by centrifugation for 5 minutes at room temperature at 2000 rpm in a tabletop centrifuge and the cells resuspended in 50 ml 10 mM MgSO$_4$. The resuspended host cells (50 µl) were mixed with 100 µl stock of each positive phage and incubated for 15 minutes at 37° C. to permit phage attachment to the cells. Approximately 500 µl LBM media was added and the mixture shaken for 2 hours at 37° C. An additional 200 µl of host cells was added and incubation continued for an additional 15 minutes at 37° C. Top agar (8 ml of 0.75% LBM agarose at 48° C.) was added after which the mixture was plated and grown overnight at 37° C.

Following overnight growth, 12 ml of lambda diluent (10 mM Tris-HCl, pH 7.5, 10 mM MgSO$_4$) was added to each plate and the plates rocked gently for 2 hours. The diluent was removed and centrifuged for 10 minutes, 4000×g, in a tabletop centrifuge. To the supernatant, 1 µl each of 1 mg/ml RNase A and 1 mg/ml DNase I were added and incubation carried out at 37° C. for 15 minutes. An equal volume of precipitation buffer (20% PEG 8000, 2M NaCl, 20 mM Tris-HCl, pH 7.5, 10 mM MgSO$_4$) was added followed by incubation on ice for one hour, after which the mixture was centrifuged at 8000×g for 20 minutes, the supernatant removed, and the pellet air dried for 10 minutes at room temperature. The pellet was resuspended in 500 µl TE, centrifuged briefly to remove particulates, and the supernatant transferred to a clean 1.65 ml epitube. Approximately 2.5 µl 20% SDS was added (with 5 minutes incubation at 65° C.), followed by addition of 2.5 µl 10 mg/ml proteinase K (with incubation for one hour at 65° C.) and 10 µl 5M NaCl. The mixture was extracted once with an equal volume of phenol:CHCl$_3$ and once with an equal volume of CHCl$_3$. An equal volume of isopropanol was added followed by incubation at −70° C. for 3 hours, after which the mixture was centrifuged for 15 minutes in an epifuge at top speed. The resulting pellet was washed with 70% ethanol, air dried, and resuspended in 100 µl TE.

EXAMPLE 2

Subcloning of the EF-1α Regulatory Sequence

To determine the size of the insert EF-1α DNA, phage DNA prepared as described in Example 1 was digested with NotI and the resulting restriction fragments separated on a 0.6% 1× TAE agarose gel. Clones 2.12 and 2.17 showed identical digestion patterns with bands of 11 kb and 4.5 kb in addition to the expected flanking lambda fragments of 19 kb and 10 kb. Clones 7.44 and 40.24 also showed identical digestion patterns with insert bands of 12 kb and 7 kb which, together with Clones 2.12 and 2.17 digest information, indicated the presence of an internal NotI restriction site in the EF-1α DNA. Insert fragments from clones 2.12 and 7.44 were subcloned as follows.

Phage DNA (60 µl) prepared as described in Example 1 was digested with NotI, after which the digested DNA was precipitated with addition of 20 µl 3M sodium acetate and 400 µl 100% ethanol. Precipitated DNA was collected by centrifugation, washed in 200 µl 70% ethanol, air dried 15 minutes, resuspended in 20 µl TE and heated to 65° C. for 10 minutes before addition of 2 µl loading buffer for electrophoresis. DNA was separated using agarose gel electrophoresis and bands of 4.5 kb, 7 kb, 11 kb, and 12 kb were cut out as agarose slices. DNA was extracted from each gel slice using the QIAGEN QIAquick gel extraction kit according to the manufacturer's suggested protocol. Band purity and concentration were estimated by separating a 5 µl aliquot of each isolated fragment on a 0.6% 1× TAE agarose gel.

Individual fragments were separately ligated to NotI digested pBluescript SW$^+$. In ligations with the 11 and 12 kb fragments, the linearized vector was treated with calf alkaline phosphatase prior to introduction of the fragment insert. Two µl of each ligation were used to electroporate 40 µl XL-1 Blue electrocompetent cells. Transformed cells were plated on LBM/carb agarose plates with 40 μl 5% X-gal in dimethylforamide (DMF) and 20 μl 0.1M IPTG per plate. Cells were incubated overnight at 37° C. and in the morning, plates were moved to 4° C. to increase intensity of blue color.

In a secondary screen, white colonies were streaked on LBM/carb agarose plates containing X-gal and IPTG, as described above, and colonies that were white the following day were grown up in 3 ml of LBM/carb overnight at 37° C. Plasmid DNA from white colonies grown overnight was prepared using a WIZARD Plus Minipreps DNA Purification System (Promega, Madison, Wis.) according to the manufacturer's suggested protocol.

Restriction analysis of the isolated plasmid DNA indicated that the 4.5 kb, 7 kb and 12 kb fragments were successfully ligated into the pBluescript SW+ vector, and the resultant plasmids were designated pSK/EF1.4.5, pSK/EF1.7 and pSK/EF1.12, respectively.

Each plasmid was then prepared using a QIAGEN midi prep kit according to the manufacturer's suggested protocol. PCR was carried out on each new vector, titrating out the template DNA and using the coding region primers (SEQ ID NOs: 4 through 11, used in pairs as described above to screen for pseudogenes lacking one or more of the various introns). Titration was performed after it was found that, at high concentrations, all three fragments were shown to include the complete EF-1α coding region suggesting possible cross contamination between the three plasmid preparations. In the titration, PCR was carried out in reactions containing 2.5 μl template DNA at a concentration of 0.001, 0.01, 0.1, 1 or 10 ng/μl, and including 2.5 μl 10× PCR Buffer (Perkin Elmer), 2.0 μl 2 mM dNTP mix, 1.5 μl 25 mM $MgCl_2$, 0.125 μl Taq polymerase (Perkin Elmer), and 11.4 μl $dH_2O$. Amplification was carried out under the following conditions: 4 minutes at 94° C., followed by 30 cycles of 1 minute at 90° C., 2 minutes at 50° C., and 4 minutes at 72° C. Results indicated that the complete EF-1α coding region was located within the 4.5 kb and 7 kb fragments.

A restriction map was generated for each insert using the Stratagene FLASH Nonradioactive Gene Mapping Kit designed for use with the Lambda FIX II® vector. Instead of using phage DNA, however, plasmid DNA excised with NotI digestion from the pSK vectors described above was used. The mapping protocol was essentially that suggested by the manufacturer. Briefly, plasmids were sequenced with M13 (SEQ ID NO: 12) and M13 reverse (SEQ ID NO: 13) primers (complementary to regions within the pBluescript SW+ multiple cloning region) to locate the T3 (SEQ ID NO: 14) and T7 (SEQ ID NO: 15) primer sequences internal to the NotI site for each insert.

| | | |
|---|---|---|
| M13 | GTAAAACGACGGCCAGT | (SEQ ID NO: 12) |
| M13rev | GGAAACAGCTATGACCATG | (SEQ ID NO: 13) |
| T3 | AATTAACCCTCACTAAAGGG | (SEQ ID NO: 14) |
| T7 | GTTAATACGACTCACTATAGGGC | (SEQ ID NO: 15) |

The T7 and 73 primers were used as probes in the gene mapping protocol. Since the EF-1α insert was shown to include an internal NotI site, the fragment pairs (4.5 kb/11 kb and 7 kb/12 kb) were predicted to include one or the other of the primer sequences and it was thus determined that the 4.5 and 12 kb inserts included the 17 primer sequence while the 7 kb insert had the T3 sequence.

The 4.5 kb and 7 kb inserts containing the EF-1α coding region were excised from the vector by NotI digest. Digested DNA was separated on an agarose gel, the separated fragments cut from the gel, and DNA isolated from each gel slice using a QIAGEN QIAquick gel extraction kit according to the manufacturer's suggested protocol. Mapping was carried out using seven different enzymes in partial restriction digests. Reaction products were separated on agarose gel, DNA was transferred to Duralon-UV Nylon membrane and probed with T3 or T7 oligonucleotides as probe. The band sizes were measured and restriction maps formulated.

Plasmid pSK/EF1.7 was sequenced with the internal primers designed originally for the PCR screen (SEQ ID NOs: 4 through 11 [primers 95-136–95-143, previously described]) to insure that the gene sequence was that of the previously identified protein. Orientation of the coding region was determined and additional primers designed that allowed sequencing to the internal NotI site. The sequence of the entire coding region was determined, which was then compared to the expected cDNA sequence described in Hayashi, et al. [supra]. Sequence analysis confirmed that the isolated DNA did, in fact, encode the same EF-1α sequences as that described by Hayashi [supra]. In addition, the sequence of the first exon was identical to the previously published hamster EF-1α cDNA sequence at the 5' end [Hayashi, supra] and seven introns were identified giving a structure similar to that known for the human homolog.

The sequence and restriction map obtained from the 7 kb fragment indicated that a portion of the 5' flanking intron and the promoter were located in the 12 kb fragment 5' to the internal NotI site. A SpeI/NotI 3 kb fragment 5' to the internal NotI site was excised from the 12 kb insert and subcloned into pBluescriptSK+ previously digested with the same enzymes and the resulting plasmid was designated pSK/EF1.3. The 3 kb fragment was mapped as described above using KpnI and ClaI in order to confirm restriction sites and sequenced using an Erase-a-Base kit (Promega, Madison, Wis.) making use of the ClaI and KpnI sites to create 5' and 3' extensions, respectively. Sequence analysis indicated regions containing the promotor, TATA box, and a 0.9 kb intron in the 5' untranslated flanking region that was the same length as the first intron in the human gene [Uetsuki, 1989, supra]. The sequence for the CHEF1 promoter and 5' intron is set out in SEQ ID NO: 1, the intron comprising nucleotides 2699 through 3641.

EXAMPLE 3

Characterization of the CHEF Regulatory DNA

Sequence upstream of and including the ATG start codon of the hamster EF-1α gene is set out in SEQ ID NO: 1. Most of the identifiable transcription factor binding sites appear to be 3' to the upstream SacI site located 1.56 kb 5' to the initiating ATG codon of the EF-1α gene. Each of the expression vectors including the CHEF1 sequences described below, however, also contain 2 kb of CHEF1 sequence 5' to the SacI site.

Sequencing indicated the presence of a perfect consensus TATA box located approximately 1 kb 5' to the initiating ATG start codon and the region between the upstream SacI site and the TATA box includes numerous potential transcription factor binding sites [Boulikas, Crit. Rev. Euk. Gene Exp. 4:117–321 (1994)], including Sp1 sites (SEQ ID NOs: 16 or 17), ATF sites (SEQ ID NO: 18), and NF-1 sites (SEQ ID NO: 19).

GGCGGG SEQ ID NO: 16
GGGCGG SEQ ID NO: 17
TGACGY(C/A)R SEQ ID NO: 18
TTGGCN$_{5-6}$(T/G)CCR SEQ ID NO: 19

Similar to the human EF-1α gene, [Uetsuki, et al., supra], there is a 943 bp intron in the 5' untranslated region (UTR) of the hamster EF-1α gene which is apparent from the location of splice donor and acceptor sequences. However, using Geneworks DNA analysis program, the sequence of the intron in the 5' UTR was found to be only 62% identical to that in the human gene. The 5' intron includes numerous potential transcription factor binding sites, roughly equal to the number of binding sites between the SacI site and the TATA box, indicating that the 5' intron my be important for optimal transcription from the EF-1α promoter.

Using Geneworks DNA Analysis Program, the CHEF1 sequence from the upstream SacI restriction site downstream to, but not including, the 5' intron sequences was found to be 64% identical to the human EF-1α sequence. A comparison of the location of Sp1 transcription factor binding sites in both the human and hamster regulatory sequences is shown in Table 1. The complete human EF-1α gene sequence [Uetsuki, et al., supra] is set out in SEQ ID NO: 29.

TABLE 1

Distance of Sp1 Sites from the TATA Box

| Hamster Nucleotide Position | Human Nucleotide Position |
|---|---|
| −424 | −335 |
| −304 | −220 |
| −183 | −208 |
| −171 | 432 |
| −151 | 476 |
| −135 | 573 |
| −26 | 581 |
| 63 | 690 |
| 156 | |
| 168 | |
| 257 | |
| 261 | |
| 425 | |
| 495 | |
| 589 | |
| 594 | |
| 688 | |

EXAMPLE 4

Construction of Expression Plasmids

Numerous plasmids utilized in subsequent examples were constructed according to the following procedures.

Plasmid pSV2-dhfr (ATCC Accession No. 37146) was digested with SphI/BamHI and a 1.8 kb fragment encoding dihydrofolate reductase (DHFR) purified (Fragment 1). The DHFR encoding fragment also included SV40 promoter/operator and polyadenylation sequences located 5' and 3', respectively, in relation to the dhfr gene. Plasmid pSL1190 (Pharmacia) was digested with HindIII, the overhanging ends filled in with Klenow, and the blunt ended DNA re-ligated to destroy the HindIII site giving plasmid pSL1190H which was then digested with SphI/BamHI and a 3.4 kb fragment purified (Fragment 2). The pSV2-dhfr 1.8 kb fragment (Fragment 1) was ligated to the pSL1190H 3.4 kb fragment (Fragment 2) to give plasmid pSL1190H-dhfr.

Plasmid pSL1190H-dhfr was modified to eliminate several restriction sites as follows. The plasmid was first digested with XbaI/NheI (giving complementary overhanging ends) and the linear plasmid re-ligated eliminating both the XbaI and NheI sites. In the second procedure, pSL1190H-dhfr was digested with HindIII, the overhanging ends filled in with Klenow, and the linear plasmid re-ligated to eliminate the HindIII site. In the third process, pSL1190H-dhfr was digested with Bg/II, the overhanging ends filled in with Klenow, and the linear plasmid re-ligated to eliminate the Bg/II site. The end result of these three steps produced plasmid pSL1190H-dhfr/NXHB, wherein XbaI, NheI, HindIII, and Bg/II sites were destroyed. Plasmid pSL1190H-dhfr/NXHB was then digested with EcoRI/BamHI and a NPB1/NPB2 linker (constructed from annealing oligonucleotides NPB1 and NPB2 [SEQ ID NOs: 20 and 21]) inserted to give plasmid pSL/dhfr/NotI having a unique NotI restriction site.

NPB1 GATCGCGGCCGCGTTTAAACGGATCC (SEQ ID NO: 20)

NPB2 AATTGGATCCGTTTAAACGCGGCCGC (SEQ ID NO: 21)

Resulting plasmid pSL/dhfr/NotI was digested with Asp718/BamHI and a 1.8 kb fragment encoding DHFR purified (Fragment 3). Plasmid pRc/CMV (Invitrogen, San Diego, Calif.) was digested with Asp718/Bg/II in order to remove CMV promoter and bovine growth hormone (BGH) polyadenylation DNA and a 3.7 kb fragment purified (Fragment 4). The 1.8 kb kb pSL/dhfr/NotI fragment encoding DHFE with SV40 promoter/operator and polyadenylation sequences (Fragment 3) was ligated to the 3.7 kb pRc/CMV fragment (Fragment 4) to give plasmid pRc/DHFR/NotI.

Plasmid pRc/CMV was digested with Asp718/XbaI and a 0.8 kb fragment encoding BGH polyadenylation DNA purified (Fragment 5). Plasmid pRc/DHFR/NotI was digested with BamHI/Asp718 and a 4 kb fragment with DHFR, SV40 promoter/operator and polyadenylation sequences purified (Fragment 6). Plasmid pCEP4 (Invitrogen, San Diego, Calif.) was digested with Bg/II/SacI and a 0.7 kb fragment encoding the CMV promoter purified (Fragment 7). The 0.8 kb pRc/CMV fragment (Fragment 5), the 4 kb pRc/DHFR/NotI fragment (Fragment 6), the 0.7 kb pCEP4 fragment (Fragment 7), and a synthetic SacI/XbaI adaptor fragment were combined in a 4-way ligation to give plasmid pDC1. The adaptor was constructed by annealing oligonucleotides SXP1 and SXP2.

SXP1 (SEQ ID NO: 22)
5'-CGTTTAGTGAACCGTCAGATCTACATAACAACATTCCTC
CTCTAAAGAAGCCCCAAGCTTGATATCTGCAGAATTCT-3'

SXP (SEQ ID NO: 23)
5'-CTAGAGAATTCTGCAGATATCAAGCTTGGGGCTTCTTTAGAG
GAGGAATGTTGTTATGTAGATCTGACGGTTCACTAAACGAGCT-3'

Plasmid pDC1 therefore includes the CMV promoter, a polylinker region, a polyadenylation site from the BGH, and the dhfr gene under control of an SV40 promoter and SV40 splice/polyadenylation sequence.

Plasmid pDC1 was digested with XhoI, a 4.5 kb fragment lacking CMV promoter and BHG poladenyaltion DNA isolated and ligated to give plasmid pDCi1. Plasmid pDCi1 was then digested with BamHi/XhoI and a 4.5 kb fragment purified (Fragment 8). The 4.5 kb pDCi1 fragment (Fragment 8) was ligated to a BamHI/SalI-digested PCR fragment encoding a partial CMV promoter sequence produced using primers 96-13 and 96-14 (plasmid pDC1 as template) to give plasmid pDCi2.

Primer 96-13 (SEQ UD NO: 24)
5'-AGTTCAGTCGACGGCGCGCCAACCCGGGAATCC
GGACGGGATCTATACATTGAATCAATATTGGCA-3'

Primer 96-14 (SEQ ID NO: 25)
ATGTCAGGATCCACGCGGAACTCCATATATGGGCTATGAACT

Plasmid pDCi2 was digested with Asp718/SpeI and a 4.2 kb fragment encoding DHFR with SV40 promoter/operator and polyadenylation sequences purified (Fragment 9) and pDC1 was digested with Asp718/SpeI and a 1.5 kb fragment comprising partial CMV promoter DNA with BGH polyadenylation signals purified (Fragment 10). The 4.2 kb pDCi2 fragment (Fragment 9) was ligated to the 1.5 kb pDC1 (Fragment 10) fragment to give plasmid pDC31. Plasmid pDC31 differed from pDC1 in that several new restriction sites, including SmaI and AscI at the 5' end of the CMV promoter were generated. Plasmid pDC31 was digested with NotI, the overhanging DNA blunt-ended using T4 polymerase and the plasmid re-ligated to eliminate the NotI site and give plasmid pDC36. Plasmid pDC36 is the same as pDC31 except that the NotI site was destroyed.

Plasmid pDC36 was digested with ApaI/BamHI, overhanging ends filled in, and the plasmid re-ligated to give pDC38. pDC38 is the same as pDC36 except that the ApaI/BamHI fragment containing the bovine growth hormone polyadenylation sequence has been removed. Plasmid pDC38 was digested with SmaI/HindIII and a 4.6 kb fragment lacking the CMV promoter DNA purified (Fragment 11).

Plasmid pSK/EF1.3 was digested with EcoRV/NotI/PvuI and a 2.9 kb fragment encoding the CHEF1 promoter and upstream DNA sequences purified (Fragment 12). Bluescript SW+II (pSK+) was digested with NotI and a 2.9 kb fragment purified (Fragment 13). The 7 kb NotI fragment from Lambda phage 7.4 was ligated to the 2.9 pSK+ fragment (Fragment 13) to give plasmid pSK/EF1.7.

Plasmid pSK+ was digested with HindIII/NotI and a 2.9 kb fragment purified (Fragment 14). Plasmid pSK/EF1.7 was digested with NotI/NcoI and a 620 bp fragment encoding part of the CHEF1 5' untranslated intron purified (Fragment 15). A 123 bp HindIII/NcoI-digested PCR fragment encoding the remainder of the 5' intron generated with primers 96-36 and 96-45 and pSK/EF1.12 as template was purified (Fragment 16).

Primer 96-36 (SEQ ID NO: 26)
GGCTTAGCTCCGAGGAGGG

Primer 96-45 (SEQ ID NO: 27)
CGTGACAAGCTTGGTTTTCACAACAC

The 2.9 kb pSK+ fragment (Fragment 14), the 620 bp pSK/EF1.7 fragment (Fragment 15), and the 123 bp HindIII/NcoI fragment (Fragment 16) were ligated to give plasmid pSK/5'EF-1 having the complete CHEF1 5' intron sequence.

Plasmid pSK/5'EF-1 was digested with HindIII/NotI and a 0.7 kb fragment encoding the 5' intron purified (Fragment 17). The 4.6 kb pDC38 fragment lacking the CMV promoter (Fragment 11), the 2.9 kb pSK/EF1.3 fragment with CHEF1 promoter and upstream sequences (Fragment 12), and the 0.7 kb pSK/5'EF-1 fragment encoding the complete 5' intron (Fragment 17) were combined in a 3-way ligation to give plasmid pDEF1 which thus contained the complete 5' CHEF1 regulatory DNA, the dhfr gene, and SV40 origin of replication which permits replication to a very high copy number in cell lines transformed with the SV40 T antigen.

Plasmid pDEF1 was digested with HindIII, the overhanging ends filled in, and the plasmid digested with NotI and a 2.6 kb fragment having CHEF1 promoter and upstream DNA sequences in addition to a partial 5' intro sequence purified (Fragment 18). Plasmid pDEF1 was digested with NotI/Asp718 and a 1.3 kb fragment encoding the remainder of the 5' intron purified (Fragment 19). Plasmid pDC38 was digested with SmaI/Asp718 and a 4 kb fragment encoding DHFR with SV40 promoter/operator and polyadenylation DNA purified (Fragment 20). The 2.6 kb pDEF1 fragment (Fragment 18), the 1.3 kb pDEF1 fragment (Fragment 19), and the 4 kb pDC38 fragment (Fragment 20) were combined in a 3 way ligation to give plasmid pDEF2. Plasmid pDEF2 in E. coli strain XL-1 Blue was deposited on Mar. 4, 1997 with the American Type Culture Collection, 10801 University Boulevard, Manassas, Va. 20110-2209, and assigned Accession Number 98343. Plasmid pDEF2 differs from pDEF1 in that the 0.3 kb HindIII/SpeI fragment 2.3 kb upstream of the CHEF1 TATA box was removed and contains only one HindIII site located in the polylinker region. pDEF2 is used in instances where the gene to be expressed includes its own polyadenylation site.

Plasmid pDEF2 was digested with Asp718/XbaI to linearize the plasmid, but which also eliminated origin of replication sequences and a 7.4 kb fragment purified (Fragment 21). Plasmid pDC1 was digested with Asp718/XbaI and a 0.8 kb fragment including replacement origin or replication DNA in addition to BGH polyadenylation sequences purified (Fragment 22). The 7.4 kb pDEF2 fragment (Fragment 21) and the 0.8 kb pDC21 fragment (Fragment 22) were combined to produce plasmid pDEF10 which differs from pDEF1 in the same manner as pDEF2 differs. Plasmid pDEF10 differs from pDEF2 in that there is a polyadenylation site from the bovine growth hormone gene on the 3' end of the polylinker region in pDEF10.

Plasmid pDEF 10 was digested with HindIII/XbaI to linearize the plasmid and an 8.2 kb fragment purified (Fragment 23). Plasmid pDC1 /MDC, a plasmid encoding the human chemokine macrophage derived chemokine (MDC), was digested with HindIII/XbaI and a 0.4 kb fragment encoding MDC purified (Fragment 24). Ligation of the 8.2 kb pDEF10 fragment (Fragment 23) with the 0.4 kb pDC1 /MDC fragment (Fragment 24) produced plasmid pDEF10/MDC.1.

Plasmid pRc/CMV was digested with BamHI, the overhanging ends filled in with Klenow, the plasmid digested with Asp718, and a 1.5 kb fragment purified (Fragment 25). Plasmid pDC1 was digested with NotI, the overhanging ends filled in with Klenow, the plasmid digested with Asp718, and a 3.9 kb fragment purified (Fragment 26). The 1.5 kb pRc/CMV fragment (Fragment 25) was ligated with the 3.9 kb pDC1 fragment (Fragment 26) to give plasmid pNCX.

Plasmid pNCX is similar to the pDC1 except that the dhfr gene is replaced with a neomycin resistance (NeoR) gene. Plasmid pNCX was digested with Asp718/PvuI and a 2.1 kb fragment purified (Fragment 27). Plasmid pDEF1 was digested with Asp718/PvuI and a 5.9 kb fragment purified (Fragment 28). The 2.1 kb pNXC fragment (Fragment 27) was ligated to the 5.9 kb pDEF1 fragment (Fragment 28) to give plasmid pNEF1. pNEF1 differs from pDEF1 in that the plasmid carries the bacterial neomycin resistance gene (NeoR) encoding resistance to neomycin or G418. Genes to be inserted into pNEF1 are generally HindIII/XbaI fragments inserted following partial HindIII digestion or 3-way ligations since the plasmid has two HindIII sites.

EXAMPLE 5

Transfection of DG44 Cells and Productivity Assay

For transfections of host DG44 cells with a single plasmid, 50–100 µg of plasmid was usually linearized by digestion with restriction enzyme PvuI or AscI. For transfections wherein two plasmids were to be introduced into CHO cells, the plasmids were left undigested. Prior to transformation plasmids were ethanol precipitated and washed twice with 70% ethanol. DNA pellets were briefly dried and resuspended in 400 µl sterile, distilled water. To the resuspended DNA was added 400 µl of sterile 2× HeBS (40 mM HEPES-NaOH, pH 7.0; 274 mM NaCl; 10 mM KCl; 1.4 mM $Na_2HPO_4$; 12 mM dextrose). Untransfected DG44 cells were cultured in DMEM/F-12 medium supplemented with hypoxanthine (0.01 mM final concentration) and thymidine (0.0016 mM final concentration), also referred to as "HT". For growth of both untransfected and transfected DG44 cells, dialyzed FBS was added to the medium to a final concentration of 5 to 10% by volume. DG44 cells were prepared for transfection by growing cultures to about 50% or less confluency in treated 150 $cm^2$ tissue culture polystyrene flasks (Corning). Cells were removed from the plastic by first aspirating the medium, washing the adherent cells once with calcium-magnesium-free phosphate buffer saline (CMF-PBS: 2.7 mM KCl; 1.5 mM $KH_2PO_4$; 137 mM NaCl; 8.1 mM $Na_2HPO_4$), adding 4 ml of a solution containing 0.0125% irradiated trypsin (Worthington Biochemical Corporation) in CMF-PBS, and incubating at 37° C. for several minutes. Media (4 ml) containing fetal bovine serum (FBS) was added, the cell concentration determined, and aliquots of $2 \times 10^7$ cells pelleted by centrifugation. Each cell pellet was washed once in CMF-PBS and resuspended in 0.8 ml of a solution containing HeBS with the desired plasmid DNA. The resuspended cells were transferred to a 0.4 cm Gene Pulser cuvette (Bio-Rad) at room temperature and placed in a Bio-Rad GenePulser electroporation apparatus. Cells were electroporated at room temperature with a capacitor discharge of 290 V and 960 µFD (9 to 11.5 msec pulse). Cells were kept in the cuvette for about 10 minutes before they were added to 10 ml DMEM/F-12 supplemented with 5–10% dialyzed FBS and HT. The kill rate was determined at this point (Trypan Blue exclusion) and typically was found to be about 50%. The cells were then pelleted by centrifugation, resuspended in 2 ml DMEM/F-12 supplemented with 5–10% dialyzed FBS and HT ("non-selective media") and seeded into 10 cm polystyrene tissue culture plates. After two days growth the cells, usually confluent at this point, were removed from the plates using trypsin as described above and seeded into 10 $cm^2$ plates at varying dilutions in DMEM/F-12 supplemented with 5–10% dialyzed FBS and without HT ("selective media"). Five and nine days later, the cells were fed with selective media. After about two weeks the transfectant colonies (typically more than 1,000 for each transfection) were removed from the plates using trypsin as described above and, after addition of selective media, the cell concentration determined. From each transfection at least two aliquots of $2 \times 10^6$ cells were added to 10 cm plates containing 10 ml selective media. The cells were grown to extinction, the time at which most of the cells have detached from the plate due to overcrowding. Supernatant from the extinct cultures were assayed by ELISA to determine the average product titer.

EXAMPLE 6

Recombinant Protein Production Using CHEF1

DG44 cells described in Example 5 were transfected with plasmids carrying the genes set out in Table 3 operably linked to the CHEF1 regulatory DNA. Bacterial strains transformed with plasmids encoding each of the genes utilized in the assays were deposited on Apr. 1, 1997, with the American Type Culture Collection, 10801 University Boulevard, Manassas, Va. 20110-2209 and assigned Accession Numbers as set out in Table 2.

TABLE 2

Accession Numbers for Plasmids

| Encoded Gene | Plasmid Designation | Accession Number |
| --- | --- | --- |
| Antibody ICM3 Heavy Chain | pDEF1/ICM3H.2 | 98381 |
| Antibody ICM3 Light Chain | pNEF1/ICM3L.3 | 98382 |
| Antibody 23F2G Heavy Chain | pDEF1/F2GH.1 | 98383 |
| Antibody 23F2G Light Chain | pNEF1/F2GL.1 | 98384 |
| Chitinase | pDEF1/CTN.1 | 98385 |
| Platelet Activating Factor Acetyl Hydrolase (PAF-AH) | pDEF2/HPH.4 | 98386 |
| Macrophage Derived Chemokine (MDC) | pDEF10/MDC.1 | 98387 |

After selection for transfectants, a pool of colonies (greater than 200) from each transfection was removed from each plate using trypsin and an identical number of cells from each transfection replated and grown to extinction. The supernatants were removed and protein expression assayed either using an ELISA or enzyme assay. The results are shown in Table 3.

TABLE 3

Protein Expression Using CHEF1 and CMV Regulatory Sequences

| | Protein Titer | |
| --- | --- | --- |
| Gene Transfected | CMV | CHEF1 |
| ICM3 H + L | 554 | 1862 |
| ICM3 H + L | 288 | 2153 |
| Hu23F2G H + L | 337 | 1848 |
| MDC | 360 | 2100 |
| PAF-AH | 590 | 6574 |
| Chitinase-1 | 3200 | 2300 |
| Chitinase-2 | 8900 | 12850 |

With the exception of the first experiment examining chitinase expression (designated Chitinase-1 in Table 3), use of the CHEF1 regulatory DNA led to significantly higher levels of protein production, with increases ranging from three-fold to eleven-fold higher than expression with the CMV promoter.

In order to determine if the decreased expression observed in the assay for chitinase was an anomaly or a repeatable result characteristic of and/or unique to chitinase, the experiment was performed a second time but using two separate transfections, as opposed to the single transfection used in the first experiment which resulted in an unusually low number of transfectants obtained. In addition, a different assay for chitinase activity was employed which was demonstrated to be more precise than the techniques used in the first experiment.

Transfections in the second attempt resulted in a number of transfectants more consistent with results previously observed using pDEF2 plasmid which in other experiments produced greater than 150% the number of transfectants with the CMV plasmid. Results from the second experiment (designated Chitinase-2 in Table 3) were internally consistent which lent further credence to the results even though

17 the observed increase in protein expression (approximately 1.4 fold) over expression with the CMV promoter was less than that observed for the other proteins previously examined.

EXAMPLE 7

Recombinant Protein Production Using CHEF1 Regulatory DNA of Differing Lengths An expression vector comprising an additional 8 kb of 5' flanking DNA from the EF-1α gene was also constructed and designated pDEF14. The plasmid pDEF14 differs from pDEF2 in that pDEF14 contains approximately 11.7 kb of hamster EF-1α 5' flanking DNA while pDEF2 contains only 3.3 kb of the same sequences. The pDEF14 plasmid also includes 4 kb of hamster 3' flanking DNA adjacent the 3' end of the DHFR expression cassette. The larger pDEF14 plasmid was constructed as described below.

Briefly, a 2.6 kb AscI/NotI CHEF1 fragment was removed from pDEF2 and an 11 kb AscI/NotI CHEF1 fragment inserted in its place. Insertion of the larger sequence first required modifying an XbaI site located 11.7 kb 5' to the EF-1α initiating ATG to an AscI site. In addition, a 4 kb blunt-ended NsiI/SalI fragment, consisting of CHEF1 flanking sequence beginning at an NsiI site 118 bp 3' to the EF-1α stop codon, was inserted into the PmeI/SalI site 3' to the DHFR expression cassette located on the 3' end of the polylinker region into which genes to be expressed are inserted. The complete 3' DNA sequence, beginning at the stop codon of the EF-1α gene, is set out in SEQ ID NO: 28. Bacteria transformed with this plasmid was deposited on Apr. 9, 1997, with the American Type Culture Collection, 10801 University Boulevard, Manassas, Va. 20110-2209 and assigned Accession Numbers 98398. The resulting pDEF14 plasmid includes unique XbaI and NotI sites along with multiple HindIII sites thereby necessitating 3-way ligation to insert a gene into the plasmid for expression. For example, a gene can be inserted into the plasmid by ligating a HindIII/XbaI fragment comprising the desired gene with a 737 bp NotI/HindIII fragment from pDEF14 and a 19.7 kb XbaI/NotI fragment from pDEF14.

18

Protein expression using this vector was compared against expression using the pDEF2 vector comprising a smaller portion of the EF-1α 5' flanking region. In preliminary experiments, DNA encoding both the heavy and light chains of the antibody 23F2G was subcloned into both pDEF2 and pDEF14 vectors and expression levels determined following transfection into DG44 cells as described above in Example 5. Genes encoding both antibody chains were arranged linearly in the vectors and expression of both genes was driven by the CHEF1 sequence in the individual plasmids. Coding regions for the two chains in each plasmid were separated by identical 4.3 kb of DNA derived from the 3' untranslated region human IgG4.

Results indicated that 23F2G expression from the larger CHEF1 sequence in pDEF14 was four fold greater than antibody expression from the smaller pDEF2 sequence. This result was surprising in that most of the identifiable pDEF14 transcription binding factor sites are also in the DNA sequence in pDEF2. It is therefore possible that one or more additional and unidentified transcription factor binding sites or enhancer sequences are located in the CHEF1 DNA in the pDEF14 plasmid. Alternatively, the larger CHEF1 DNA may confer the benefit of increased transcription as a result of some property of the 3' DNA sequence.

Numerous modifications and variations in the invention as set forth in the above illustrative examples are expected to occur to those skilled in the art. Consequently only such limitations as appear in the appended claims should be placed on the invention.

---

What is claimed is:

1. A purified and isolated hamster EF-1α transcriptional regulatory DNA selected from the group consisting of:
   a) the DNA consisting of the sequence as set forth as SEQ ID NO: 1 and
   b) a hamster DNA which hybridizes to the DNA molecule of SEQ ID NO: 1 at 65° C. in 2× sodium chloride/sodium acetate (SSC) buffer.

2. The regulatory DNA according to claim 1 comprising the nucleic acid sequence shown as SEQ ID NO: 1.

3. The regulatory DNA according to claim 1 comprising a fragment of the nucleic acid sequence shown as SEQ ID NO: 1 which promotes transcription of a gene operatively linked to the regulatory DNA.

4. The regulatory DNA according to claim 3 comprising a sequence from about nucleotide 2114 to about nucleotide 3656 in the nucleotide sequence shown in SEQ ID NO: 1.

5. A host cell comprising the regulatory DNA according to any one of claims 1 through 4 wherein said regulatory DNA is not operatively linked to EF-1α coding sequences.

6. A vector comprising the regulatory DNA according to any one of claims 1 through 4 wherein said regulatory DNA is not operatively linked to EF-1α coding sequences.

7. A host cell transformed or transfected with the vector according to claim 6.

8. A chimeric polynucleotide comprising the regulatory DNA of claim 1 operatively linked to a protein coding DNA sequence, said protein coding DNA sequence encoding a protein other than hamster EF-1α.

9. The chimeric polynucleotide according to claim 8 wherein the regulatory DNA comprises the nucleic acid sequence shown as SEQ ID NO: 1.

10. The chimeric polynucleotide according to claim 8 wherein the regulatory DNA comprises a fragment of the nucleic acid sequence shown as SEQ ID NO: 1, wherein the fragment promotes transcription of a gene operatively linked to the regulatory DNA.

11. The chimeric polynucleotide according to claim 10 wherein the regulatory DNA comprises from about nucleotide 2114 to about nucleotide 3656 in the nucleotide sequence shown as SEQ ID NO: 1.

12. The chimeric polynucleotide according to claim 8 wherein said protein coding DNA sequence encodes a protein endogenous to hamster cells other than EF-1α.

13. The chimeric polynucleotide according to claim 8 wherein the DNA sequence encodes a protein heterologous to hamster cells.

14. A host cell transformed or transfected with the chimeric polynucleotide according to any one of claims 8 through 13.

15. An expression plasmid comprising the chimeric polynucleotide according to any one of claims 8 through 13.

16. The expression plasmid according to claim 15 further comprising the nucleic acid sequence set out as SEQ ID NO: 28.

17. The expression plasmid according to claim 16 wherein the nucleic acid sequence set out as SEQ ID NO: 28 is positioned 3' with respect to the chimeric polynucleotide.

18. A host cell transformed or transfected with the expression plasmid according to claim 15.

19. A host cell transformed or transfected with the expression plasmid according either claim 16 or 17.

20. A plasmid designated pDEF2.
21. A plasmid designated pDEF14.
22. A plasmid designated pDEF1./ICM3H.2.
23. A plasmid designated pNEF1/ICM3L.3.
24. A plasmid designated pDEF1/F2GH.1.
25. A plasmid designated pNEF1/F2GL.1.
26. A plasmid designated pDEF1/CTN.1.
27. A plasmid designated pDEF2/HPH.4.
28. A plasmid designated pDEF10/MDC.1.
29. A host cell transformed or transfected with the plasmid according to any one of claims 20 through 28.

* * * * *

UNITED STATES PATENT AND TRADEMARK OFFICE
CERTIFICATE OF CORRECTION

PATENT NO. : 5,888,809
DATED : March 30, 1999
INVENTOR(S) : Daniel S. Allison

It is certified that error appears in the above-indentified patent and that said Letters Patent is hereby corrected as shown below:

Col. 17, line 16: Please add "and", between 95-136 and 95-193.

Col. 39, line 47: Please delete "in", and insert - -as- -.

Col. 40, line 54, after "according": Please insert - -to- -.

Signed and Sealed this

Seventeenth Day of April, 2001

*Attest:*

NICHOLAS P. GODICI

*Attesting Officer*    *Acting Director of the United States Patent and Trademark Office*